US008649836B2

(12) United States Patent
Shimizu et al.

(10) Patent No.: US 8,649,836 B2
(45) Date of Patent: Feb. 11, 2014

(54) FLUORESCENCE SENSOR, NEEDLE-TYPE FLUORESCENCE SENSOR, AND METHOD FOR MEASURING ANALYTE

(75) Inventors: Etsuro Shimizu, Shiojiri (JP); Kazuya Matsumoto, Kamiina-gun (JP); Ryo Ota, Kamiina-gun (JP); Atsushi Matsumoto, Hadano (JP)

(73) Assignee: Terumo Kabushiki Kaisha, Tokyo (JP)

( * ) Notice: Subject to any disclaimer, the term of this patent is extended or adjusted under 35 U.S.C. 154(b) by 82 days.

(21) Appl. No.: 13/271,732

(22) Filed: Oct. 12, 2011

(65) Prior Publication Data
US 2012/0029328 A1 Feb. 2, 2012

Related U.S. Application Data

(63) Continuation of application No. PCT/JP2010/056730, filed on Apr. 8, 2010.

(30) Foreign Application Priority Data

Apr. 13, 2009 (JP) ................................. 2009-097330
Apr. 13, 2009 (JP) ................................. 2009-097331

(51) Int. Cl.
 *A61B 5/1455* (2006.01)
(52) U.S. Cl.
 USPC .......................................... 600/316; 600/310
(58) Field of Classification Search
 USPC .................................................. 600/309–344
 See application file for complete search history.

(56) References Cited

U.S. PATENT DOCUMENTS

| 4,755,667 A | 7/1988 | Marsoner et al. |
| 5,039,490 A | 8/1991 | Marsoner et al. |
| 5,517,313 A | 5/1996 | Colvin, Jr. |
| 5,965,875 A | 10/1999 | Merrill |

(Continued)

FOREIGN PATENT DOCUMENTS

| AU | 2004 201 752 A1 | 5/2004 |
| CN | 1178006 A | 4/1998 |

(Continued)

OTHER PUBLICATIONS

Abstract of International Publication No. WO 96/26429 A1, dated Aug. 29, 1996.

(Continued)

*Primary Examiner* — Eric Winakur
*Assistant Examiner* — Marjan Fardanesh
(74) *Attorney, Agent, or Firm* — Scully, Scott, Murphy & Presser, P.C.

(57) ABSTRACT

A needle-type fluorescence sensor that measures glucose based on fluorescence produced by excitation light is provided. The needle-type fluorescence sensor includes a needle body section including a sensor portion disposed in a needle distal end portion and metal lines disposed from the sensor portion to a needle proximal end portion, and a connector which is integrated with the needle body section and in which the metal lines extend. The sensor portion includes a silicon substrate having first and second principal surfaces, a PD device that converts fluorescence into an electric signal, an LED device that transmits fluorescence and emits excitation light, and an indicator layer that interacts with an analyte under the excitation light to produce fluorescence. The PD device, the LED device, and the indicator layer overlap with each other above the first principal surface of the silicon substrate.

27 Claims, 13 Drawing Sheets

(56) References Cited

U.S. PATENT DOCUMENTS

| | | | |
|---|---|---|---|
| 6,330,464 B1 * | 12/2001 | Colvin et al. | 600/316 |
| 6,331,438 B1 | 12/2001 | Aylott et al. | |
| 6,882,875 B1 | 4/2005 | Crowley | |
| 7,221,455 B2 | 5/2007 | Chediak et al. | |
| 7,388,110 B2 | 6/2008 | Ochiai et al. | |
| 7,524,985 B2 | 4/2009 | Ochiai et al. | |
| 2004/0234417 A1 * | 11/2004 | Schienle et al. | 422/82.08 |
| 2005/0221277 A1 * | 10/2005 | Kawanishi | 435/4 |
| 2005/0245799 A1 * | 11/2005 | Brauker et al. | 600/347 |
| 2005/0258438 A1 * | 11/2005 | Arik et al. | 257/88 |

FOREIGN PATENT DOCUMENTS

| | | |
|---|---|---|
| CN | 1298483 A | 6/2001 |
| JP | 11-500825 | 1/1999 |
| JP | 2003-515163 | 4/2003 |
| JP | 2005-010114 | 1/2005 |
| JP | 2005-227155 | 8/2005 |
| JP | 2006-509547 | 3/2006 |
| WO | WO 2006/090596 A1 | 8/2006 |

OTHER PUBLICATIONS

Abstract of International Publication No. WO 01/38857 A1, dated May 31, 2001.

International Search Report dated Jun. 1, 2010 issued in PCT/JP2010/056730.

European Search Report dated Nov. 5, 2012 from corresponding European Patent Application No. 10 76 4498.1.

Colvin Jr., A.E., et al., "A Novel Solid-State Oxygen Sensor", Johns Hopkins APL Technical Digest, vol. 17, No. 4 (1996), pp. 377-385.

Chinese Office Action mailed Feb. 5, 2013 in corresponding Chinese Patent Application No. 201080016664.7 together with English language translation.

Japanese Office Action mailed Mar. 5, 2013 in corresponding Japanese Patent Application No. 2011-536657.

* cited by examiner

FLUORESCENCE SENSOR, NEEDLE-TYPE FLUORESCENCE SENSOR, AND METHOD FOR MEASURING ANALYTE

CROSS REFERENCE TO RELATED APPLICATION

This application is a continuation application of PCT/JP2010/056730 filed on Apr. 8, 2010 and claims benefit of Japanese Applications No. 2009-097330 filed in Japan on Apr. 13, 2009, and No. 2009-097331 filed in Japan on Apr. 13, 2009, the entire contents of which are incorporated herein by this reference.

BACKGROUND OF THE INVENTION

1. Field of the Invention

The present invention relates to a fluorescence sensor that is a minute-fluorescence photometer for measuring the concentration of an analyte in a living body, a needle-type fluorescence sensor including the fluorescence sensor, and a method for measuring the analyte by using the fluorescence sensor, and particularly to a fluorescence sensor fabricated by using semiconductor manufacturing technologies and micro-machine manufacturing technologies, a needle-type fluorescence sensor including the fluorescence sensor, and a method for measuring the analyte by using the fluorescence sensor.

2. Description of the Related Art

A variety of analyzing apparatuses have been developed to check the presence of an analyte, that is, a substance to be measured in a liquid, or measure the concentration thereof. For example, there has been a known fluorescence photometer that quantifies the concentration of an analyte by injecting a solution to be measured containing a fluorescent dye and the analyte, the fluorescent dye changing its nature in response to the presence of the analyte to emit fluorescence, into a fixed-capacity, transparent container, irradiating the container with excitation light, and measuring the intensity of the fluorescence from the fluorescent dye.

On the other hand, a small-sized fluorescence photometer specializing in specific analyte detection includes a light source, a photodetector, and an indicator layer containing a fluorescent dye that interacts with a specific analyte in a solution to be measured. When the indicator layer, which the analyte in the solution to be measured can enter, is irradiated with excitation light from the light source, the fluorescent dye in the indicator layer emits fluorescence, the amount of which depends on the concentration of the specific analyte in the solution to be measured, and the photodetector receives the fluorescence. The photodetector is a photoelectric conversion device and outputs an electric signal according to the amount of received light. The electric signal is used to determine the concentration of the analyte in the solution to be measured.

In recent years, to measure a specific analyte in a tiny amount of specimen, a minute-fluorescence photometer fabricated by using semiconductor manufacturing technologies and micro-machine manufacturing technologies has been proposed.

For example, U.S. Pat. No. 5,039,490 discloses a fluorescence sensor 110 shown in FIGS. 1 and 2. It should be noted that an analyte 2 is diagrammatically illustrated in the following figures.

As shown in FIGS. 1 and 2, the fluorescence sensor 110 includes a transparent support substrate 101 through which excitation light E from an external light source can pass, a photoelectric conversion device unit 103, which is a photo-detector for converting fluorescence F into an electric signal, an optical plate-shaped unit 105 having a light collecting function section 105A for collecting the excitation light E, an indicator layer 106 that interacts with the analyte 2 to emit fluorescence F when the excitation light E is incident, and a cover layer 109.

The photoelectric conversion device unit 103 has a photoelectric conversion device formed in a substrate 103A made, for example, of silicon. The substrate 103A does not transmit the excitation light E. In consideration of this fact, the fluorescence sensor 110 has a void region (transparent zone) 120, through which the excitation light E can pass, around the photoelectric conversion device unit 103.

That is, only the excitation light E that passes through the void region 120 and impinges on the optical plate-shaped unit 105 is collected by the effect of the optical plate-shaped unit 105 in the indicator layer 106 in the vicinity of an upper portion of the photoelectric conversion device unit 103. The collected excitation light E2 interacts with the analyte 2 that has entered the indicator layer 106, and fluorescence F is produced. Part of the produced fluorescence F is incident on the photoelectric conversion device unit 103, which produces a current or voltage signal or any other suitable type of signal proportional to the intensity of the fluorescence, that is, the concentration of the analyte 2. It should be noted that the excitation light E is not incident on the photoelectric conversion device unit 103 due to the effect of a filter (not shown) disposed on the photoelectric conversion device unit 103.

As described above, the fluorescence sensor 110 is configured in such a way that a photodiode, which is the photoelectric conversion device unit 103, is formed on the transparent support substrate 101 and in the substrate 103A having the void region 120, which is a passage of the excitation light E, and the optical plate-shaped unit 105 and the indicator layer 106 are disposed above the substrate 103A.

In the known fluorescence sensor 110 described above, however, the void region 120, which is a passage of the excitation light E, and the photoelectric conversion device unit 103 are disposed in the same plane. As a result, increasing the area of the void region 120, which is a passage of the excitation light E, to introduce more excitation light E into the indicator layer 106 results in decrease in the area of the photoelectric conversion device unit 103 and hence does not increase the sensitivity of the fluorescence sensor. Conversely, increasing the area of the photoelectric conversion device unit 103 to increase the detection sensitivity thereof results in decrease in the area of the void region 120, which is a passage of the excitation light E, and hence decrease in the amount of excitation light E to be introduced into the indicator layer 106, which does not increase the sensitivity of the fluorescence sensor either. That is, in the fluorescence sensor having the laminate structure described above, it is difficult to achieve high detection sensitivity.

On the other hand, a needle-type sensor is a sensor for determining the concentration of an analyte, that is, a substance to be measured, in the blood or a body fluid in a subject by puncturing the subject with a needle distal end portion so that a sensor unit, which is a fluorescence sensor, is inserted into the body of the subject. A short-term indwelling, needle-type sensor can continuously determine the concentration of a substance to be measured in the body of a subject for a predetermined period, for example, one week.

The needle-type fluorescence sensor shown in FIGS. 3 and 4 is a biosensor 210 disclosed in International Publication No. 06/090596. It should be noted that an analyte 2 is diagrammatically illustrated in the following figures. The biosensor 210 includes a needle-shaped hollow container 212, a carrier tube 214 inserted into the hollow container 212, and an optical fiber 218, an end portion of which is inserted into the carrier tube 214. The hollow container 212 has one sharp end and one open end. A plurality of through holes 220 are provided through a side portion of the hollow container 212. The carrier tube 214 is formed of a rounded thin film. A sensor unit 216 is formed only of an indicator section, which is an end portion of the optical fiber 218 covered with a ruthenium organic complex thin film 224, which is a fluorescent dye.

The analyte 2 enters the sensor unit 216 through the through holes 220. The biosensor 210 uses the optical fiber 218 to irradiate the sensor unit 216 with excitation light from a light source (not shown) external to the biosensor 210, uses the optical fiber 218 to receive fluorescence, the amount of which depends on the concentration of the analyte, produced in the sensor unit 216. A photodetector (not shown) external to the biosensor 210 analyzes the fluorescence.

On the other hand, U.S. Pat. Nos. 7,388,110 and 7,524,985 disclose saccharide measuring sensors that are implanted in the body of a subject. Each of the sensors uses a fluorescence sensor substance and an indicator unit using the fluorescence sensor substance. The fluorescence sensor substance is obtained by copolymerizing a fluorescent monomer compound and a polymerizable monomer, the fluorescent monomer compound having a hydrophobic moiety which is bonded to a saccharide to emit fluorescence and to which a hydrophilic group is introduced and the polymerizable monomer having a (meth)acrylamide residue.

SUMMARY OF THE INVENTION

A fluorescence sensor according to an embodiment of the present invention includes a base member having first and second principal surfaces, a light emitting device that emits excitation light, an indicator layer that interacts with an analyte in a living body under the excitation light to produce fluorescence, and a photoelectric conversion device that converts the fluorescence into an electric signal. The photoelectric conversion device, the light emitting device, and the indicator layer overlap with each other above the first principal surface of the base member.

A needle-type fluorescence sensor according to another embodiment of the present invention including the fluorescence sensor described above includes a needle body section including a sensor portion, which is the fluorescence sensor disposed in a needle distal end portion and a plurality of metal lines disposed from the sensor portion to a needle proximal end portion, and a connector which is integrated with the needle body section and in which the plurality of metal lines extend. The sensor portion includes a base member having first and second principal surfaces, a light emitting device that emits excitation light, an indicator layer that interacts with an analyte in the living body under the excitation light to produce fluorescence, and a photoelectric conversion device that converts the fluorescence into an electric signal. The photoelectric conversion device, the light emitting device, and the indicator layer overlap with each other above the first principal surface of the base member.

A method for measuring an analyte according to still another embodiment of the invention includes an excitation light irradiation step in which excitation light emitted from a light emitting device is introduced into an indicator layer, a fluorescence emission step in which the indicator layer interacts with the analyte under the excitation light to produce fluorescence, and a photoelectric conversion step in which the fluorescence produced in the indicator layer passes through the light emitting device, impinges on a photoelectric conversion device, and is converted into an electric signal.

DETAILED DESCRIPTION OF THE PREFERRED EMBODIMENTS

First Embodiment

A fluorescence sensor 10 according to a first embodiment of the present invention will be described below with reference to the drawings.

Figure 5:
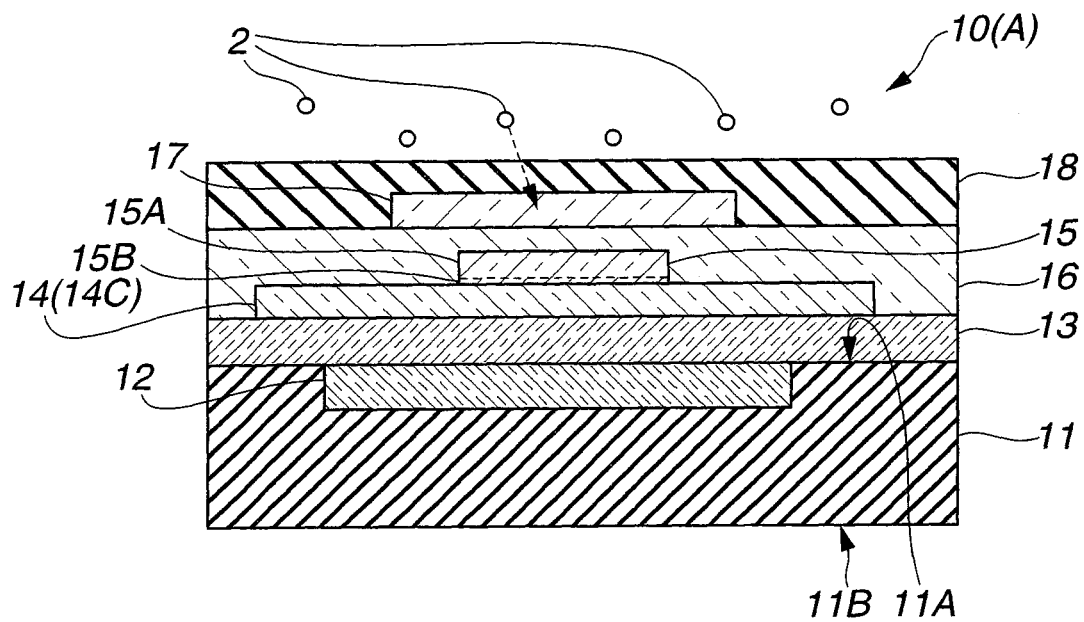
FIG. 5 is a diagrammatic view showing a schematic cross-sectional configuration of a fluorescence sensor according to a first embodiment.
Figure 6:
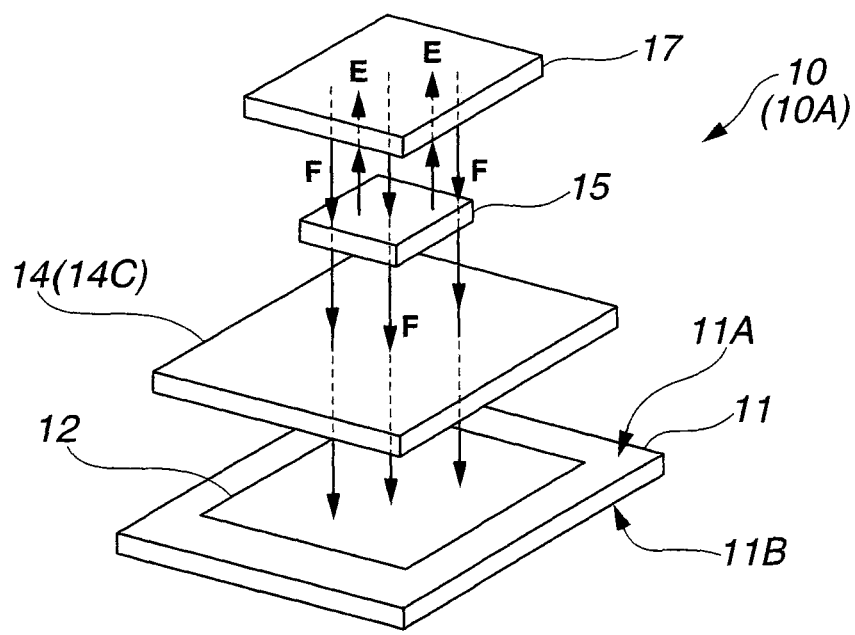
FIG. 6 is an exploded view for describing the schematic configuration of the fluorescence sensor according to the first embodiment.

As shown in FIGS. 5 and 6, the fluorescence sensor 10 of the present embodiment has a structure in which a silicon substrate 11, which is a base member and has a first principal surface 11A and a second principal surface 11B, a photodiode (hereinafter also referred to as "PD") device 12, which is a photoelectric conversion device, a silicon oxide film ($SiO_2$ film) 13, a filter 14, a light emitting diode (hereinafter also referred to as "LED") device 15, which is a light emitting device that transmits fluorescence, an epoxy resin film 16, an indicator layer 17, and a light blocking layer 18 are sequentially stacked above the first principal surface 11A of the silicon substrate 11. At least portions of the PD device 12, the filter 14, the LED device 15, and the indicator layer 17 are disposed in the same region above the first principal surface 11A of the silicon substrate 11. The "... disposed in the same region" means that at least part of the fluorescence from the indicator layer 17 passes through the LED device 15 and then impinges the PD device 12 and represents that the PD device 12 is isolated from the indicator layer 17 by the LED device 15.

In other words, the LED device 15 and the filter 14 are disposed above the PD device 12 formed on the first principal surface 11A of the silicon substrate 11. The indicator layer 17 is disposed above the LED device 15 and the filter 14. The PD device 12, the filter 14, the LED device 15, and the indicator layer 17 overlap with each other above the first principal surface of the silicon substrate 11. The fluorescence produced in the indicator layer 17 passes through the LED device 15 and the filter 14 and is converted into an electric signal in the PD device 12.

It is more preferred that central portions of the PD device 12, the filter 14, the LED device 15, and the indicator layer 17 be disposed in the same region above the first principal surface 11A of the silicon substrate 11.

That is, the fluorescence sensor 10 has a structure totally different from those of known fluorescence sensors in that the LED device 15, which is a light emitting device that transmits the fluorescence from the indicator layer 17, is used.

As will be described later, when the light blocking layer 18 of the fluorescence sensor 10 comes into contact with the blood or a body fluid in a living body, the analyte 2 passes through the light blocking layer 18 and enters the indicator layer 17.

The silicon substrate 11 is a base member having the PD device 12 formed on the first principal surface 11A. The silicon substrate 11 can be made thin approximately to several tens of micrometers in a manufacturing step, which is still thick enough not to transmit excitation light and fluorescence. To form the PD device 12 as a photoelectric conversion device on the surface of the base member, the base member is preferably a single-crystal silicon substrate. Depending on how to manufacture the PD device 12, the silicon substrate can be replaced with other semiconductor substrates or other variety of materials.

The PD device 12 is a photoelectric conversion device that converts fluorescence into an electric signal. The photoelectric conversion device is not necessarily a PD device but can be selected from a variety of photoelectric conversion devices, such as a photoconductor and a phototransistor (hereinafter also referred to as "PT"). A photodiode or a phototransistor can achieve the highest, highly stable fluorescence detection sensitivity and hence particularly preferable because the fluorescence sensor 10 can show excellent detection sensitivity and detection precision.

The silicon oxide film ($SiO_2$ film) 13 is a first protective film having a thickness ranging from several tens to several hundreds of nanometers and may alternatively be a silicon nitride film (SiN film) or a composite laminate film formed of a silicon oxide film and a silicon nitride film.

The filter 14 is an absorptive optical filter that does not transmit excitation light E emitted from the LED device 15 but transmits fluorescence F having a wavelength longer than that of the excitation light E. That is, in the fluorescence sensor 10, the filter 14, which absorbs excitation light having a wavelength shorter than that of fluorescence but transmits fluorescence, is located between the PD device 12 and the LED device 15. The following description will be made with reference to a case where the fluorescence F has a wavelength of, but not limited to, approximately 460 nm and the excitation light E has a wavelength of, but not limited to, approximately 375 nm.

Figure 7:
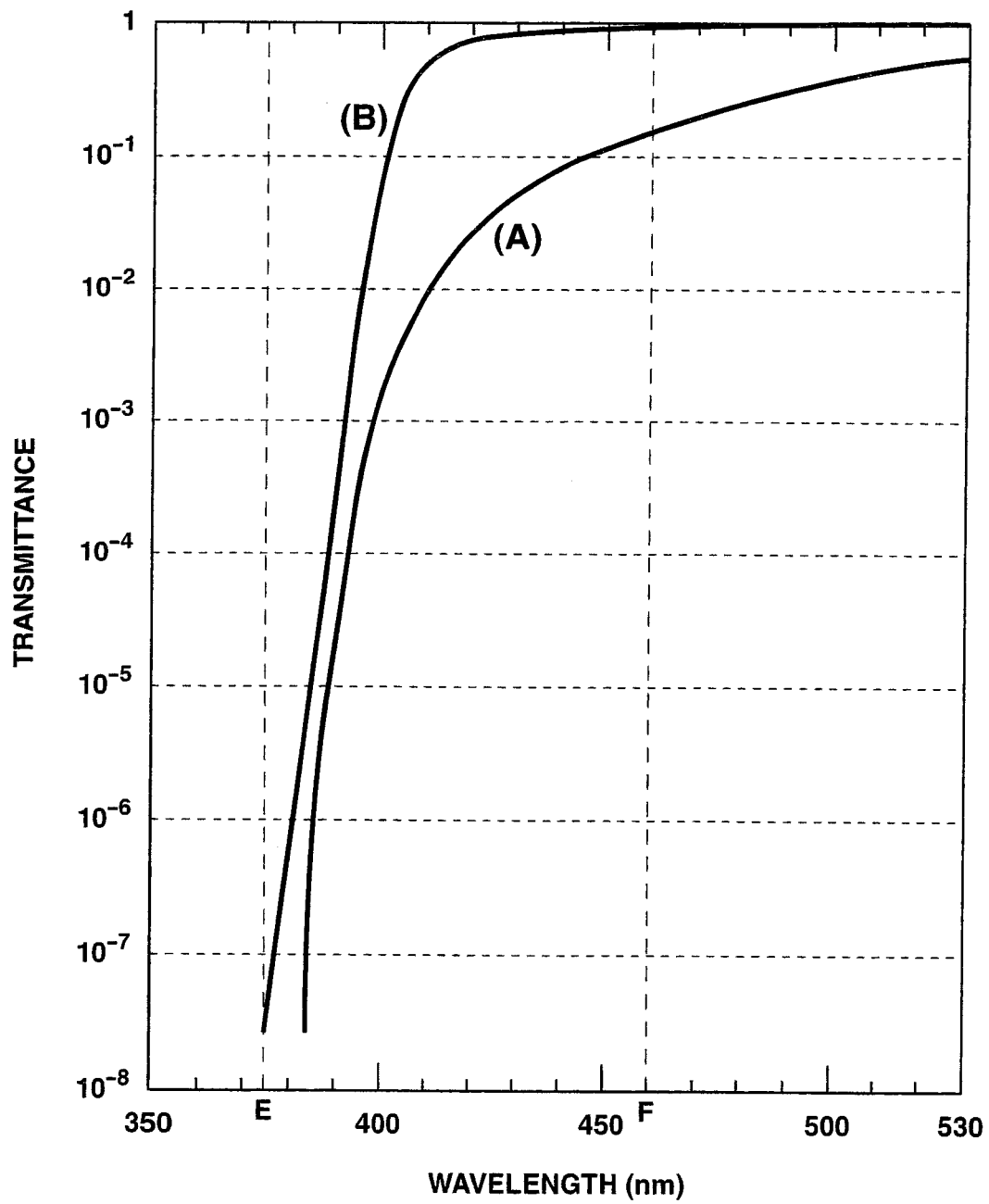
FIG. 7 is a graph showing dependence on wavelength of optical transmittance of a silicon film or a silicon carbide film, which is a filter in the fluorescence sensor according to the first embodiment.

FIG. 7 shows how much light passes through a silicon film or a silicon carbide (SiC) film having a predetermined film thickness in relation to wavelength (optical transmittance). In FIG. 7, the horizontal axis represents wavelength and the vertical axis represents optical transmittance. The line (A) represents a 0.5 μm-thick silicon film, and the line (B) represents a 360 μm-thick silicon carbide film.

As shown in FIG. 7, for the silicon film (A) and the silicon carbide film (B), the transmittance is $10^{-7}$ or lower at the wavelength of the ultraviolet excitation light E of approximately 375 nm, whereas the transmittance is $10^{-1}$ or higher, that is, 10% or higher at the wavelength of the fluorescence F of approximately 460 nm, which means that both the films (A) and (B) have transmittance selectivity, the ratio of the transmittance at one wavelength to the transmittance at another wavelength, of $10^6$ or higher.

In particular, when a silicon film is used as the filter 14, a thickness of 1 μm suffices for the function of the filter 14. In this case, the filter 14 can be integrally formed above the silicon substrate 11 in a known semiconductor manufacturing step. The filter 14 may be made of non-doped silicon or preferably be formed of a polysilicon film or an amorphous silicon film which has a thickness ranging from sub-micrometer to several micrometers and to which phosphorus or any other suitable impurity is doped.

Alternatively, gallium phosphide (GaP) can preferably be used as the material of the filter 14 because its transmittance is low at the wavelength of excitation light shorter than approximately 375 nm but high at the wavelength of fluorescence of 460 nm.

The fluorescence sensor 10 achieves satisfactory excitation light blocking and fluorescence transmission characteristics when the filter 14 is a light absorptive one. In this case, the filter 14 can be disposed in the fluorescence sensor 10 at a low cost because a monolayer filter 14 is simply disposed above the PD device 12. In particular, the filter 14, when it is a light absorptive monolayer made of silicon or silicon carbide, can provide satisfactory excitation light blocking and fluorescence transmission characteristics as well as excellent stability and controllability in manufacture.

The LED device 15 is a light emitting device that emits excitation light and transmits fluorescence. The light emitting device is not limited to an LED device, but any device that especially transmits fluorescence may be selected from a variety of light emitting devices, such as an organic EL device, an inorganic EL device, and a laser diode device. An LED device is preferred because, for example, it excels in fluorescence transmittance, light emission efficiency, has broad excitation light wavelength selectivity, and emits a very small amount of light having a wavelength different from that of ultraviolet excitation light.

Further, from the fluorescence transmittance point of view, a particularly preferable example of the LED device 15 is an ultraviolet emission LED device made of gallium nitride-based compound semiconductor 15B formed on a sapphire substrate 15A, which is a second substrate. That is, the sapphire substrate 15A and the gallium nitride-based compound semiconductor 15B excel in fluorescence transmittance.

Examples of the gallium nitride-based compound semiconductor 15B may include GaN, AlInGaN, and InGaN- and AlGaN-based materials. An ultraviolet emission LED may alternatively be made, for example, of ZnO-, AlN-, or diamond-based material.

The LED device 15 has an LED light emitting portion made of the gallium nitride-based compound semiconductor 15B and formed on one surface of the sapphire substrate 15A, and excitation light from the LED light emitting portion also passes through the sapphire substrate 15A and exits through the other surface, which is opposite the surface where the LED light emitting portion is formed. The sapphire substrate 15A, which transmits fluorescence, can be made thin to approximately several tens of micrometers, as in the case of the silicon substrate 11.

When an organic EL device that transmits fluorescence is used as the light emitting device, the organic EL device can be integrally formed in a wafer process above the silicon substrate, which is the base member. That is, an organic EL device that transmits fluorescence can be fabricated by stacking an aluminum ultrathin-film cathode, a light emitting layer made of a low-molecular-weight aluminum complex or a high-molecular-weight it conjugate polymer, and an ITO (Indium Tin Oxide) film anode in a semiconductor manufacturing step. Therefore, the fluorescence sensor 10 using an organic EL device as the light emitting device can be made thin and integrally formed for cost reduction.

The epoxy resin film 16 is a second protective film. Other examples of the second protective film may include a silicone resin, which is used to glue the LED device 15 to the filter 14, and a transparent amorphous fluororesin. The material of the second protective film is selected from materials providing electrical insulation, water blockage, satisfactory transmission of the excitation light E and the fluorescence F, and other factors.

Another important feature of the second protective film in the fluorescence sensor 10 is that only a very small amount of fluorescence is to be produced under the excitation light. The feature of producing only a very small amount of fluorescence is, of course, important for all the transparent materials used in the fluorescence sensor 10 except the indicator layer 17.

The indicator layer 17 produces fluorescence when interacting with the analyte 2 having entered the indicator layer 17 under excitation light, that is, produces fluorescence, the amount of which depends on the concentration of the analyte 2. The layer thickness of the indicator layer 17 is set at approximately several tens of micrometers. The indicator layer 17 is made of a base material containing a fluorescent dye that emits fluorescence, the intensity of which depends on the amount of analyte 2, that is, the concentration of the analyte in a specimen. The base material of the indicator layer 17 preferably shows transparency, which allows the excitation light from the LED device 15 and the fluorescence from the fluorescent dye to pass through the indicator layer 17 in a satisfactory manner. The fluorescent dye may be the analyte 2 itself present in the specimen.

The fluorescent dye is selected in accordance with the type of the analyte 2 and can be any fluorescent dye that reversibly changes the amount of fluorescence produced in accordance with the amount of analyte 2. For example, to measure the concentration of hydrogen ions or carbon dioxide in a living body, a hydroxypyrene trisulfonic acid derivative can be used. To measure saccharides, a phenylboronic acid derivative having a fluorescent residue can be used. To measure potassium ions, a crown ether derivative having a fluorescent residue can be used.

To measure saccharides, such as glucose, in a living body, a protein that is bonded to a fluorescent dye, such as a ruthenium organic complex, a fluorescent phenylboronic acid derivative, and fluorescein, and will be reversibly bonded to glucose can, for example, be used. Examples of the ruthenium organic complex may include complexes of ruthenium and 2,2'-bipyridine, 1,10-phenanthroline, 4,7-diphenyl-1,10-phenanthroline, 4,7-dimethyl-1,10-phenanthroline, 4,7-disulfonated diphenyl-1,10-phenanthroline, 2,2'-bi-2-thiazoline, 2,2'-bithiazole, 5-bromo-1,10-phenanthroline, and 5-chloro-1,10-phenanthroline. Further, the ruthenium organic complex can be replaced, for example, with an organic complex of osmium, iridium, rhodium, rhenium, or chrome. As the fluorescent phenylboronic acid derivative, a compound containing two units of phenylboronic acid and anthracene as a fluorescent residue particularly shows high detection sensitivity.

As described above, the fluorescence sensor 10 of the present invention can be used in a variety of applications, such as an oxygen sensor, a glucose sensor, a pH sensor, an immunity sensor, and a microorganism sensor by selecting a fluorescent dye appropriately.

The base material of the indicator layer 17 is, for example, a hydrogel, which readily contains water, with any of the fluorescent dyes described above contained therein or bonded thereto. Examples of the component of the hydrogel may include an acrylic hydrogel prepared by polymerizing monomers such as methyl cellulose, polysaccharide like dextran, (meth)acrylamide, methylol acrylamide, or hydroxy ethyl acrylate; or an urethane-based hydrogel prepared from polyethylene glycol and diisocyanate. A liquid containing a fluorescent dye can also be used as the indicator layer 17. When a liquid or a fluid sol is used as the indicator layer 17, the liquid or the fluid sol is sealed in a space surrounded, for example, by a solid wall.

To detect saccharides in blood or a body fluid, the indicator layer 17 may be made of a fluorescence sensor substance obtained by copolymerizing a fluorescent monomer compound (fluorescent dye) and a polymerized monomer having a (meth)acrylamide residue. A preferable example of the fluorescent monomer compound may be 9,10-bis(methylene) [[N-(ortho-borono-benzyl)methylene]-N-[(acryloylpolyoxyethylene)carbonylamino]-n-hexamethylene]-2-acetylanthracene (hereinafter referred to as "F-PEG-AAm").

Being suitable for a long-term continuous monitoring, the fluorescence sensor 10 can in particular be preferably used as a glucose sensor for quantitatively monitoring the concentration of a saccharide in a living body.

The indicator layer 17 is joined to the epoxy resin film 16 via an adhesive layer (not shown) made, for example, of a silane coupling agent. In an alternative structure, no epoxy resin film 16 is disposed, but the indicator layer 17 may be directly joined to the surface of the LED device 15. Still alternatively, the indicator layer 17 or part thereof may be buried in a recess formed in the surface of the LED device 15, that is, the surface of the sapphire substrate 15A that is opposite the surface where the gallium nitride-based compound semiconductor 15B is formed.

The light blocking layer 18, which is the top layer, is disposed on the upper side of the indicator layer 17 and has a thickness of several tens of micrometers or smaller. The light blocking layer 18 comes into contact with a body fluid or blood. The light blocking layer 18 not only prevents any excitation light and fluorescence from leaking out of the fluorescence sensor 10 but also prevents external light from entering the fluorescence sensor 10.

To block light other than that originating from the LED device 15, that is, to block unwanted light that would enter the fluorescence sensor 10 and possibly degrade a fluorescence signal, the light blocking layer 18 desirably covers the entire fluorescence sensor 10 as well as the indicator layer 17. The light blocking layer 18 is made of a material that does not prevent the analyte 2 from passing through the light blocking layer 18 and reaching the indicator layer 17. When the fluorescence sensor 10 is used to analyze an analyte in an aqueous solution, the light blocking layer 18 is preferably a porous metal or ceramic, or a composite material obtained by mixing carbon black, carbon nanotubes, or any other suitable non-light-transmissive fine particles into the hydrogel used to form the indicator layer 17. Although not shown, the circumferential surfaces of the LED device 15, the filter 14, and the PD device 12 in the fluorescence sensor 10 are preferably coated with the same material as that of the light blocking layer 18 or a resin having a light blocking capability with which carbon black is blended, or deposited with a metal film having a light blocking capability.

In the fluorescence sensor 10 having the structure described above, the fluorescent dye in the indicator layer 17 is irradiated with the excitation light E from the LED device 15. The fluorescence F emitted from the fluorescent dye passes through the LED device 15 and the filter 14, reaches the PD device 12, and is converted into an electric signal.

A method for manufacturing the fluorescence sensor 10 of the present embodiment will now be briefly described.

Figure 8A:
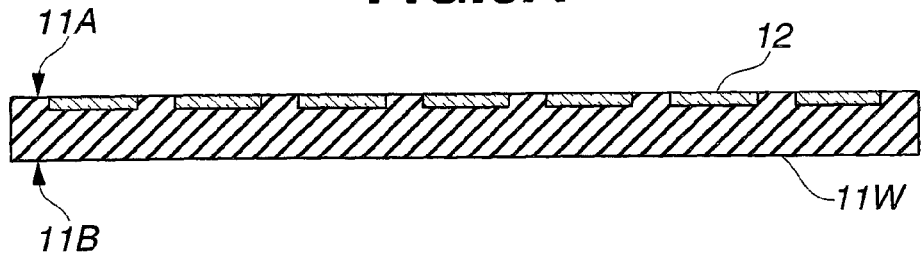
FIG. 8A is a cross-sectional diagrammatic view for describing a method for manufacturing the fluorescence sensor according to the first embodiment.
Figure 8B:
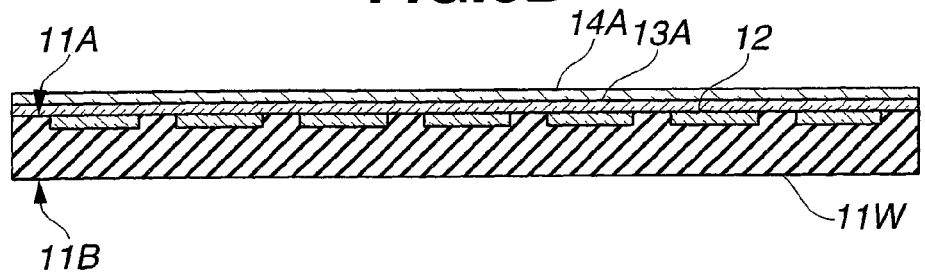
FIG. 8B is another cross-sectional diagrammatic view for describing the method for manufacturing the fluorescence sensor according to the first embodiment.

First, a large number of PD devices 12 are formed on the first principal surface 11A of a silicon wafer 11W, which will form the silicon substrate 11 (FIG. 8A). The silicon oxide film 13 having a thickness ranging from several tens to several hundreds of nanometers, which will form the first protective film, is then formed on the surface of the PD devices 12. The filter 14 made, for example, of polycrystalline silicon or amorphous silicon is formed on the surface of the silicon oxide film 13 (FIG. 8B). The steps described above are the same as semiconductor manufacturing front-end steps, and the large number of PD device 12 and other components are formed all together on the silicon wafer 11W, which are then separated into individual devices.

Subsequently, the LED device 15 or any other suitable light emitting device is disposed in a predetermined position on the filter 14 of each of the separated devices. To dispose the LED device 15, a variety of methods can be used, such as an adhesion method using an optically transparent acrylic or silicone resin, or any other suitable resin, a flip-chip bonding method, a plasma activated joining method in which a joint interface is activated by plasma or any other suitable processing for joining, and other variety of joining methods.

The epoxy resin film 16 is formed, as required, as the second protective film on the LED devices 15, and then the indicator layer 17 is joined via a silane coupling agent or any other suitable adhesive layer. The adhesive layer for the indicator layer 17 is also made of a material that produces no fluorescence when irradiated with excitation light. In the case of the fluorescence sensor 10, the indicator layer 17 is prepared as a gel film having a thickness of 25 μm by polymerizing fluorescent dye-containing F-PEG-AAm and acrylamide and methylene-bis-acrylamide under the presence of sodium persulfate and N,N,N',N'-tetramethylethylenediamine. Finally, the light blocking layer 18 is formed on the indicator layer 17. The fluorescence sensor 10 is thus completed.

It should be noted that a wafer level packaging technology can alternatively be used as the method for manufacturing the fluorescence sensor 10 of the present embodiment.

Figure 8C:
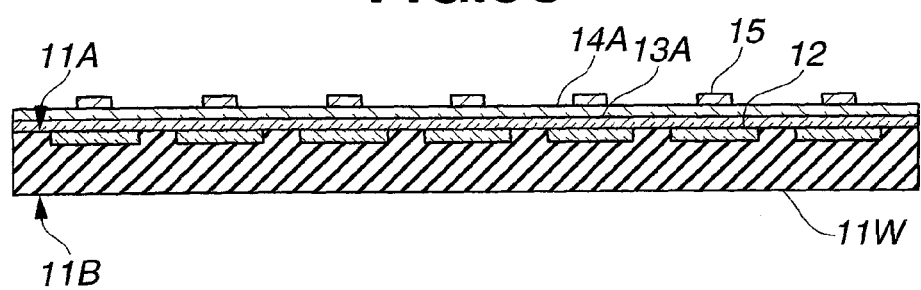
FIG. 8C is another cross-sectional diagrammatic view for describing the method for manufacturing the fluorescence sensor according to the first embodiment.
Figure 8D:
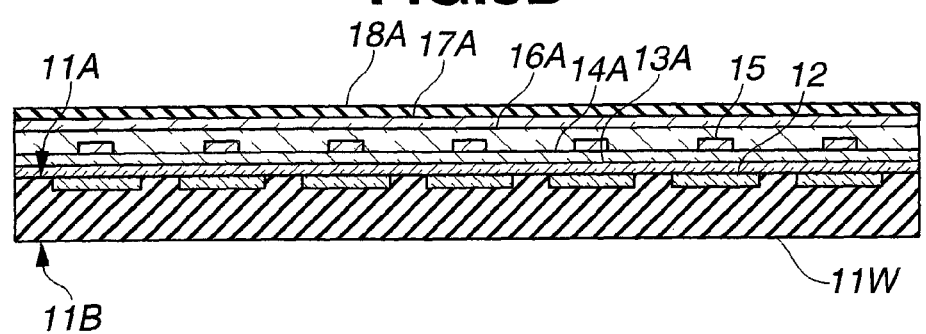
FIG. 8D is another cross-sectional diagrammatic view for describing the method for manufacturing the fluorescence sensor according to the first embodiment.
Figure 8E:
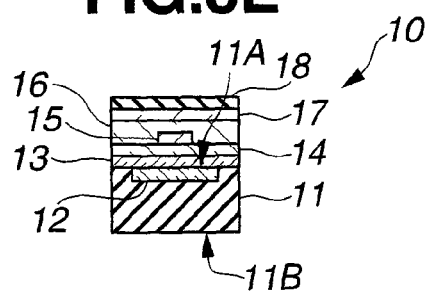
FIG. 8E is another cross-sectional diagrammatic view for describing the method for manufacturing the fluorescence sensor according to the first embodiment.

That is, as shown in FIG. 8A, a PD device formation step of forming a large number of PD devices 12 on the first principal surface 11A of the silicon wafer 11W, which is a first wafer, is carried out in the same manner as a semiconductor manufacturing front-end step. Thereafter, as shown in FIG. 8B, a filter formation step of forming a silicon oxide film 13A and a filter film 14A is carried out. On the other hand, an LED device formation step of forming a large number of LED devices 15 all together on a sapphire substrate, which is a second wafer, and dividing the second wafer is carried out. Thereafter, as shown in FIG. 8C, an LED device joining step of joining the LED devices 15 obtained by dividing the second wafer to the filter film 14A on the first wafer is carried out. Further, as shown in FIG. 8D, an indicator film formation step of forming an indicator film 17A and a light blocking film 18A is carried out. Finally, as shown in FIG. 8E, a dividing step of dividing the first wafer into individual fluorescence sensors 10 is carried out.

Alternatively, as the method for manufacturing the fluorescence sensor 10 of the present embodiment, an indicator film formation step of forming the indicator film 17A and the light blocking film 18A on the second wafer is carried out after the LED device formation step performed on the second wafer, and the second wafer is divided into LED devices, each of which is provided with the indicator film. A dividing step of dividing the first wafer into fluorescence sensors 10 may be carried out after each of the LED devices with the indicator film is joined to the first wafer.

Still alternatively, as the method for manufacturing the fluorescence sensor 10 of the present embodiment, the dividing step may be carried out after the first wafer with the filter film is joined to the second wafer with the indicator film. This manufacturing method requires electrode portions for electrically wiring the LED devices and other components to be exposed along the cut surfaces produced when the joined wafers are divided.

The operation of the fluorescence sensor 10 of the present embodiment will be described with reference to FIGS. 5 and 6. When the fluorescence sensor 10 or at least the outer surface of the light blocking layer 18 indwells in a living body, the analyte 2 in the body fluid or the blood passes through the light blocking layer 18 and enters the indicator layer 17.

In the fluorescence sensor 10, the LED device 15 emits excitation light. For example, the pulse width of the light emitted from the LED device 15 ranges from 10 to 100 ms. The magnitude of pulsed current ranges from approximately 1 to 100 mA. The central wavelength of the excitation light is approximately 375 nm. The excitation light is emitted, for example, every 30 seconds.

The excitation light from the LED device 15 passes through the epoxy resin film 16 and enters the indicator layer 17. That is, the excitation light emitted from the LED device 15 is introduced into the indicator layer 17 in an excitation light irradiation step. In the following fluorescence emission step, the indicator layer 17 interacts with the analyte 2 under the excitation light to produce fluorescence, the intensity of which is proportional to the amount of analyte 2. The fluorescent dye, for example, F-PEG-AAm, in the indicator layer 17 produces fluorescence having a peak wavelength of 460 nm in response to the excitation light having a wavelength of 375 nm. The filter 14 blocks the excitation light from the LED device 15 from entering the PD device 12 to the extent that the PD device 12 can make measurement without any problem.

The fluorescence from the indicator layer 17 passes through the epoxy resin film 16, the LED device 15, the filter 14, and the silicon oxide film 13 and impinges on the PD device 12. The fluorescence from the indicator layer 17 then undergoes photoelectric conversion in the PD device 12, and light-induced electric charge is produced. That is, in a photoelectric conversion step, at least part of the fluorescence produced in the indicator layer 17, most of the fluorescence in practice, passes through the LED device 15, is guided to the PD device 12, and is converted into an electric signal.

In the fluorescence sensor 10, a signal detection circuit (not shown) detects the amount of analyte in the form of a current resulting from the light-induced electric charge from the PD device 12 or a voltage resulting from accumulated light-induced electric charge.

It should be noted that the signal detection circuit can perform more precise signal detection by using a FDA (Floating Diffusion Amplifier)-based method, which is a known method used in an image sensor.

In the fluorescence sensor 10, the excitation light and the fluorescence pass through the LED device 15, that is, the front and rear surfaces of the sapphire substrate 15A in which the gallium nitride-based compound semiconductor 15B is formed. To improve how efficiently the excitation light and the fluorescence are used, a structure for preventing optical reflection may be formed on each of the front and rear surfaces of the LED device 15. A representative example of the anti-reflection structure is a λ/4 film (quarter wavelength film), or nano-protrusion structures smaller than the wavelength of the light in question may alternatively formed on each of the surfaces.

A signal from the PD device 12 that receives fluorescence emitted from the indicator layer 17 free of the analyte 2 and a signal from the PD device 12 that receives no fluorescence are called offset outputs. The signal detection circuit subtracts the offset outputs from signal components and uses the resultant signal as analyte information. A signal output proportional to the amount of actually present analyte 2 is thus produced. For example, the signal detection circuit reads and stores a signal immediately before excitation light emission, subsequently reads a fluorescence signal, and reads the difference between the two signals as a signal again.

Although not shown, a temperature sensor is disposed in the vicinity of the PD device 12. A temperature signal from the temperature sensor, as well as the fluorescence signal from the PD device 12, is also transferred to the signal detection circuit through metal wiring. The signal detection circuit corrects fluorescence intensity data, for example, by using the temperature information to produce a signal representing the concentration of the analyte 2. The temperature sensor is preferably a semiconductor temperature sensor formed on the silicon substrate 11 on which the PD device 12 is formed.

In the fluorescence sensor 10 including the PD device 12 as a photoelectric conversion device, the PD device 12 can also be used as the temperature sensor. That is, the PD device 12 can be used as the temperature sensor when no photoelectric conversion operation is carried out.

As described above, in the fluorescence sensor 10 of the present embodiment, the excitation light emitted from the LED device 15 toward the indicator layer 17 excites the fluorescent dye in the indicator layer 17 to cause the fluorescent dye to emit fluorescence. The portion of the fluorescence that is directed toward the LED device 15 mostly passes through the LED device 15 except the portions reflected off the interface between the LED device 15 and the indicator layer 17 and absorbed when passing through the LED device 15, further passes through the filter 14, and reaches the PD device 12. That is, the PD device 12 in the fluorescence sensor 10 receives the fluorescence having passed through the LED device 15 and produces a fluorescence signal. On the other hand, the excitation light emitted from the LED device 15 toward the PD device 12 is reflected off or absorbed by the filter 14, and the light reflected off the filter 14 passes through the LED device 15, reaches the indicator layer 17, and excites the fluorescent dye.

The fluorescence sensor 10 has significantly higher excitation light and fluorescence usage efficiency as well as higher detection sensitivity than those of known fluorescence sensors. Further, it is not necessary to design any geometric optical path for excitation light and fluorescence in the fluorescence sensor 10, but the components are simply stacked into a multilayer. The fluorescence sensor 10 is therefore readily manufactured because no positioning of designed optical path patterns, which is required to be carried out with higher precision when the sensor becomes smaller, is required. Further, since the fluorescence sensor 10 allows the excitation light intensity to be greater and the area of the photoelectric conversion device to be larger than those in known fluorescence sensors, the fluorescence sensor 10 excels known fluorescence sensors in detection sensitivity and detection precision.

Moreover, since the fluorescence sensor 10 does not require any geometric optical path design, which tends to be complicated and needs to be carried out precisely, but has the indicator layer 17 and the LED device 15 stacked in parallel to each other, the indicator layer 17 is less likely to be irradiated with the excitation light in a non-uniform manner, whereby a homogeneous fluorescence signal, weak though it is, is produced.

Further, the fluorescence sensor 10 is a small-sized fluorescence photometer having integrated light source (light emitting device), photodetector (photoelectric conversion device), and indicator layer, unlike a known fluorescence sensor having a light source and/or a photodetector external thereto.

As described above, the method for measuring an analyte by using the fluorescence sensor of the present embodiment includes the excitation light irradiation step in which the excitation light emitted from the light emitting device is introduced into the indicator layer, the fluorescence emission step in which the indicator layer interacts with the analyte under the excitation light to produce fluorescence, and the photoelectric conversion step in which the fluorescence produced in the indicator layer passes through the light emitting device, impinges on the photoelectric conversion device, and is converted into an electric signal.

The method for manufacturing the fluorescence sensor 10 of the present embodiment contributes to stable manufacture of the fluorescence sensor 10 in volume. The manufactured fluorescence sensor 10 is characterized by high detection sensitivity, a small size, excellent detection sensitivity and detection precision, satisfactory manufacturing yield, and a low price.

Second Embodiment

A fluorescence sensor 10A according to a second embodiment of the present invention will be described. The fluorescence sensor 10A of the present embodiment is similar to the fluorescence sensor 10 of the first embodiment. The same components therefore have the same reference characters and no description thereof will be made.

The filter 14 in the fluorescence sensor 10 of the first embodiment is a filter formed, for example, of a silicon monolayer film, but a filter 14C (see FIGS. 5 and 6) in the fluorescence sensor 10A of the present embodiment is a multiple interference filter. That is, the filter 14C is formed by dividing a silicon monolayer film or any other similar film into thin films and stacking the divided thin films so that the resultant filter has a multiple interference effect as well as an absorption effect.

Figure 9A:
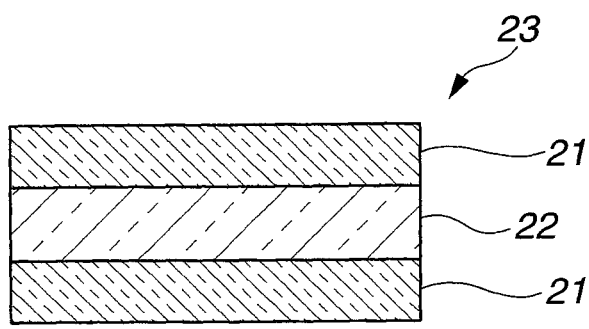
FIG. 9A is a cross-sectional diagrammatic view for describing the structure of a filter in the fluorescence sensor of the first embodiment.
Figure 9B:
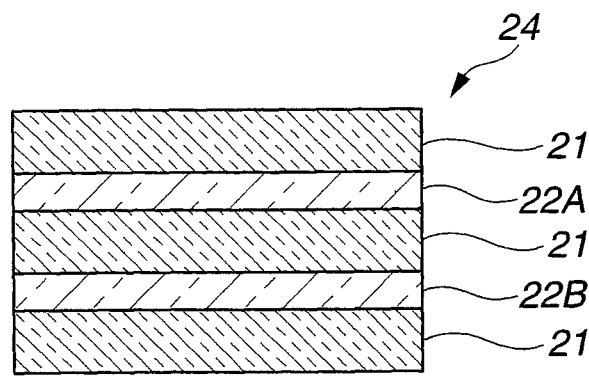
FIG. 9B is a cross-sectional diagrammatic view for describing the structure of a filter in a fluorescence sensor according to a second embodiment.

The filter 14C having a multiple interference effect will be described below with reference to FIGS. 9A and 9B. FIG. 9A is a schematic cross-sectional view of a monolayer filter, and FIG. 9B is a schematic cross-sectional view of the filter of the present embodiment. That is, FIG. 9A shows an example of a monolayer filter 23 obtained by sandwiching a silicon monolayer 22 between silicon oxide layers 21 having a refractive index lower than that of the silicon monolayer 22, and FIG. 9B shows an example of a multiple interference filter 24 obtained by dividing the silicon layer 22 into two silicon layers 22A and 22B and sandwiching each of them between the silicon oxide layers 21.

That is, the multiple interference filter 14C in the fluorescence sensor 10A has a structure in which each of the silicon layers 22A and 22B is sandwiched between the silicon oxide layers 21 having a refractive index lower than that of the silicon layer 22, as shown in FIG. 9B. The relationship between the wavelength λ at which the optical transmittance is maximized by the interference effect and a layer thickness T is expressed by the following equation (1) (free-end-to-free-end condition):

$$T = \lambda \times K / (2 \times n) \quad \text{(Equation 1)}$$

where K represents a natural number and n represents the refractive index of silicon.

Similarly, the condition under which the transmittance is minimized, that is, the transmittance has a bottom value, is expressed by the following equation (2):

$$T = \lambda \times (2 \times K - 1)/(4 \times n) \quad \text{(Equation 2)}$$

The equations (1) and (2) are used to select a layer thickness that substantially satisfies the following equation (3). The resultant interference effect allows the filter characteristics to be more desirable, that is, to block more excitation light but transmit more fluorescence.

$$\lambda_f \times K1/(2 \times n_f) = \lambda_s \times (2 \times K2 - 1)/(4 \times n_s) \quad \text{(Equation 3)}$$

where the subscript f represents fluorescence and the subscript s represents excitation light. K1 and K2 are integers.

For example, when the following values are substituted into the equation (3): $\lambda_f = 460$ nm, $n_f = 4.58$, $\lambda_s = 375$ nm, and $n_s = 6.71$, the following equation (4), which is an indeterminate equation, is obtained:

$$(2 \times K2 - 1)/K1 = 3.6 \quad \text{(Equation 4)}$$

When K1=2 is substituted into the equation (4), K2=4.1 is obtained, which is close to a solution in natural numbers.

When K1=2 is substituted into the equation (1), the thickness of each of the silicon layers is calculated to be 101.5 nm. That is, when the total thickness of the silicon film of the filter 14C is 500 nm, the silicon film may be divided into five 100 nm-thick layers.

Silicon oxide (SiO$_2$) having a refractive index lower than that of silicon is interposed between the silicon layers formed of the multiple silicon films. In this case, the silicon oxide layers also follow the optimization conditions: the equation (1) for the peak condition and the equation (2) for the bottom condition. For silicon oxide (n=1.474 at 375 nm and n=1.46 at 460 nm), the following equation (5), which is an indeterminate equation, is obtained (fix-end-to-fixed-end condition).

$$(2 \times K2 - 1)/K1 = 2.48 \quad \text{(Equation 5)}$$

The equation (5) shows that K2=3 and K1=2.02 are close to solutions in natural numbers. In this case, the thickness of each of the silicon oxide layers is 315 nm.

That is, when a silicon film having a total thickness of 500 nm is used as the filter, the silicon film may be divided into five 100 nm-thick silicon films, and a 315 nm-thick silicon oxide layer may be sandwiched therebetween. The silicon oxide may be replaced with silicon nitride (SiN).

The fluorescence sensor 10A of the present embodiment provides the advantageous effect provided by the fluorescence sensor 10 of the first embodiment. Further, since the fluorescence sensor 10A includes the multiple interference filter 14C, which excels in blocking excitation light and other light having wavelengths different from that of fluorescence and has more satisfactory fluorescence transmission characteristics, the signal-to-noise ratio of a detected signal in the fluorescence sensor 10A can be improved as compared to that in the fluorescence sensor 10.

That is, the fluorescence sensor 10A can show optimum excitation light blockage and fluorescence transmission characteristics because the filter 14C has multiple functions of light absorption, light transmission, and multiple interference. In particular, since the filter 14C formed of a multilayer film includes silicon layers and silicon oxide layers or silicon nitride layers, the following advantageous effects are provided: The thickness of each of the layers that form the multilayer film are controlled in a satisfactory manner; the optical characteristics are reproduced in an excellent manner; and the multilayer film can be fabricated in a manufacturing step compatible to standard semiconductor manufacturing technologies and micro-machine manufacturing technologies.

As described above, the filter in the fluorescence sensor 10A of the present embodiment, which is a multiple interference filter formed of silicon layers and silicon oxide layers or silicon nitride layers, reflects and/or absorbs the excitation light having a wavelength shorter than that of the fluorescence and transmits the fluorescence.

The filter 14 described above is an absorptive filter, but the filter is not limited thereto. Alternatively the filter 14 may be a notch filter that sharply cuts off only excitation light, a long-pass filter that is also referred to as an edge filter or a short-cut filter and transmits only the light having a wavelength longer than that of excitation light, a diffractive filter, or a polarization-type filter. Further, a combination of any of the variety of filters described above may be used as the filter.

Moreover, a high-concentration impurity diffused layer may be formed on the surface of the PD device 12 to absorb excitation light. In this case, the diffused layer corresponds to the filter 14. The conditions under which such a diffused layer is formed are, of course, set in such a way that the intensity of the signal representing fluorescence, the absorption length of which is long, does not greatly decrease but remains substantially unchanged.

Third Embodiment

A fluorescence sensor 10B according to a third embodiment of the present invention will be described. The fluorescence sensor 10B of the present embodiment is similar to the fluorescence sensor 10 of the first embodiment. The same components therefore have the same reference characters and no description thereof will be made.

Figure 10:
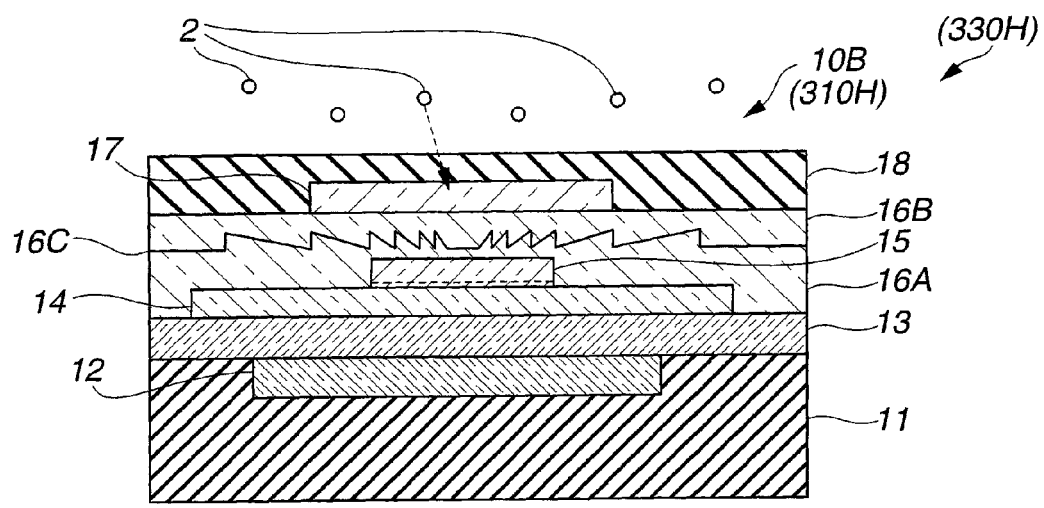
FIG. 10 is a diagrammatic view showing a schematic cross-sectional configuration of a fluorescence sensor according to a third embodiment.

As shown in FIG. 10, the fluorescence sensor 10B of the present embodiment is a fluorescence sensor in which a Fresnel lens 16C, which is a light collecting section, is additionally formed between the LED device 15 and the indicator layer 17. The Fresnel lens 16C is obtained by forming a predetermined convex and concave pattern at the interface between two types of epoxy resin films 16A and 16B having different refractive indices. The Fresnel lens 16C provides an advantageous effect of efficiently directing the excitation light from the LED device 15 toward the indicator layer 17 and efficiently collecting the fluorescence from the indicator layer 17 into the PD device 12. The Fresnel lens 16C may alternatively be replaced with a lens or any other suitable component that serves as a light collecting section but is separate from the epoxy resin film 16.

The fluorescence sensor 10B shown in FIG. 10 has the Fresnel lens 16C, which is a light collecting section, disposed between the LED device 15 and the indicator layer 17. In replacement of or in addition to the Fresnel lens 16C, the fluorescence sensor may be configured to have a light collecting section disposed in a first insulating film (silicon oxide film 13) between the PD device 12 and the filter 14.

Figure 1:
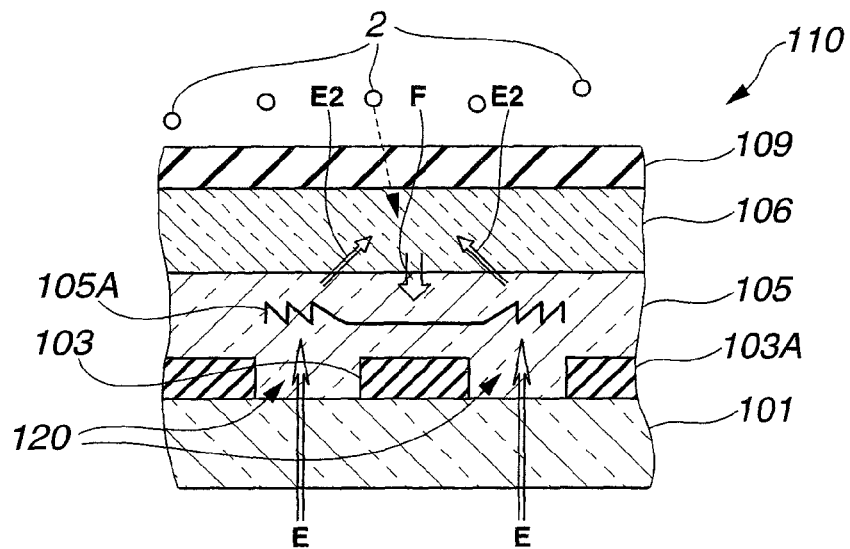
FIG. 1 is a descriptive diagram showing a schematic cross-sectional structure of a known fluorescence sensor.
Figure 2:
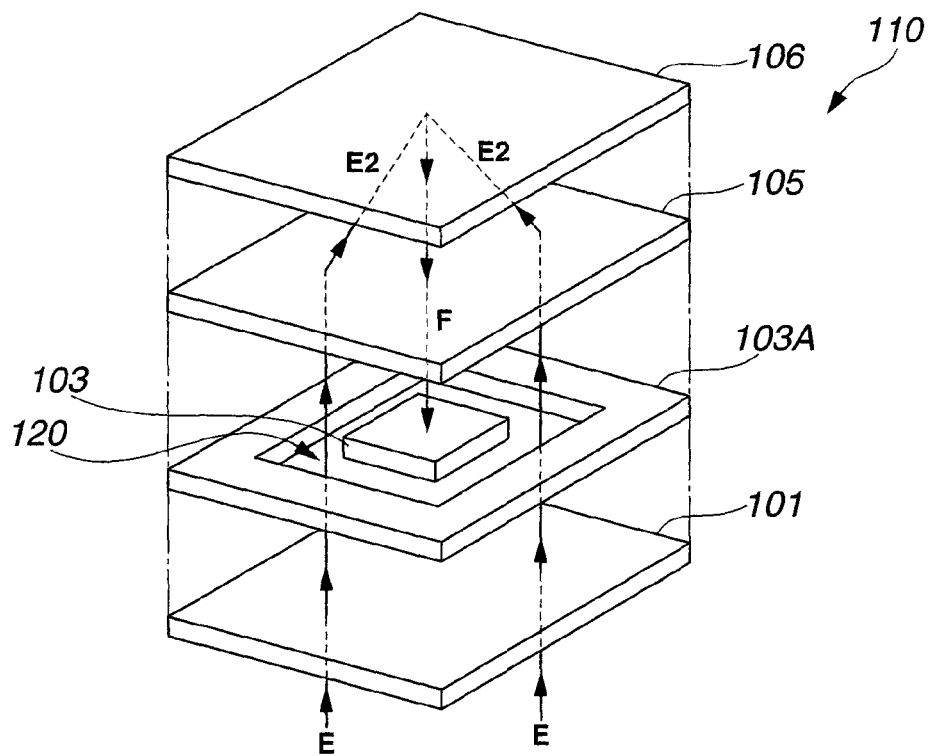
FIG. 2 is an exploded view for describing the schematic structure of the known fluorescence sensor.
Figure 3:
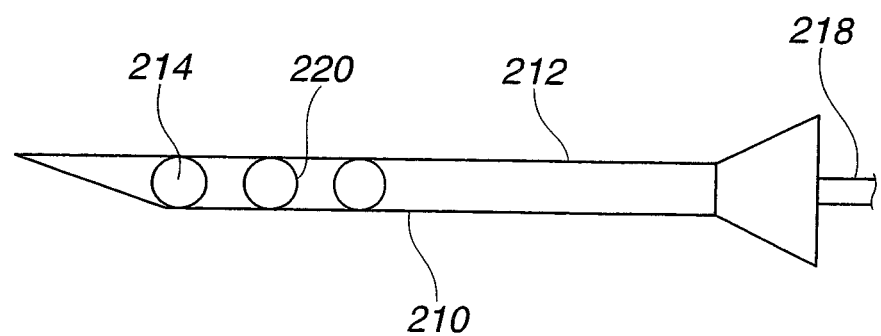
FIG. 3 is a side view showing a schematic configuration of a known needle-type fluorescence sensor.
Figure 4:
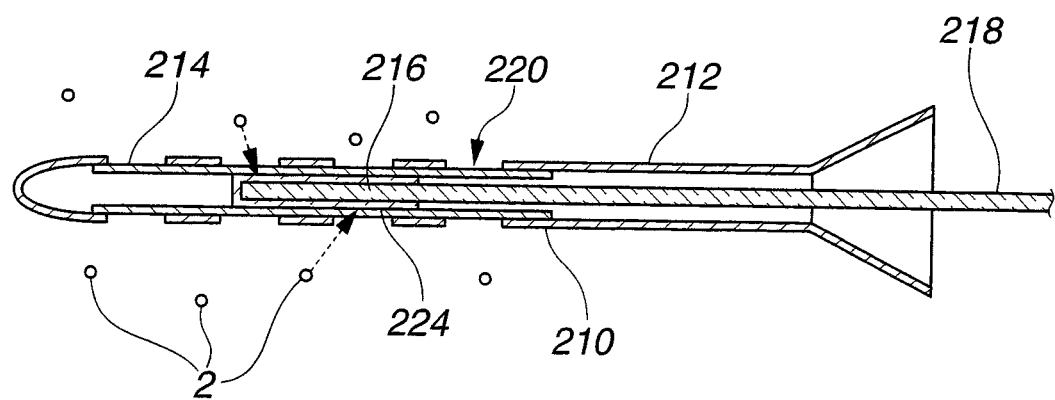
FIG. 4 is a cross-sectional view showing a schematic cross-sectional configuration of the known needle-type fluorescence sensor.

The fluorescence sensor 10B of the present embodiment is a more sensitive fluorescence sensor than the fluorescence sensor 10 because of the presence of the Fresnel lens 16C, which is a light collecting section, in addition to the advantageous effect provided by the fluorescence sensor 10 of the first embodiment. In the fluorescence sensor 110 disclosed in U.S. Pat. No. 5,039,490, the light collecting function section 105A is essential to collect the excitation light E having passed through the frame-shaped void region 120 into the indicator layer 106 disposed in correspondence with a central portion of the frame shape, as shown in FIG. 2. In contrast, the fluorescence sensor of the present invention does not essentially require a light collecting section to irradiate the indicator layer 17 with the excitation light E, as shown in FIG. 6. Further, since the fluorescence produced in the indicator layer 17 passes through the LED device 15 and is converted into the electric signal in the PD device 12, a light collecting section is not an essential component in this case as well.

Fourth Embodiment

A fluorescence sensor 10C according to a fourth embodiment of the present invention will be described. The fluorescence sensor 10C of the present embodiment is similar to the fluorescence sensor 10 of the first embodiment. The same components therefore have the same reference characters and no description thereof will be made.

As shown in FIG. 5 and other figures, in the fluorescence sensor 10 of the first embodiment and other fluorescence sensors, the light blocking layer 18, which the analyte 2 can enter, is disposed on the indicator layer 17. In contrast, the fluorescence sensor 10C of the present embodiment allows the analyte 2 to enter the indicator layer 17 through a side surface thereof via the light blocking layer 18 from the left when the fluorescence sensor 10C is viewed from the front, as shown in FIG. 11.

Figure 11:
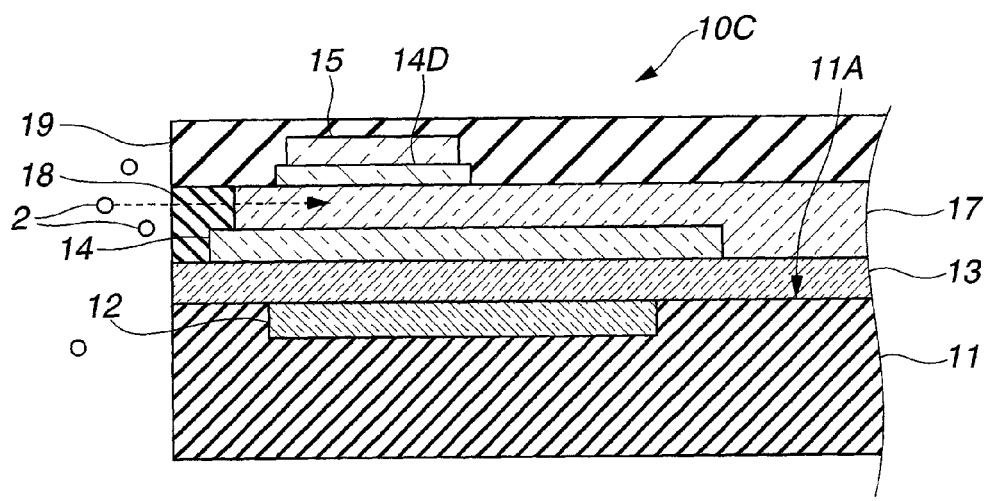
FIG. 11 is a diagrammatic view showing a schematic cross-sectional configuration of a fluorescence sensor according to a fourth embodiment.

As shown in FIG. 11, in the fluorescence sensor 10C of the present embodiment, the indicator layer 17 is disposed above the PD device 12 formed on the first principal surface 11A of the silicon substrate 11, and the LED device 15 is disposed above the indicator layer 17. The fluorescence produced in response to the analyte 2 having entered the indicator layer 17 through the side surface thereof is incident on the PD device 12 and converted into an electric signal. Further, the filter 14, which reflects and/or absorbs the excitation light having a wavelength shorter than that of the fluorescence and transmits the fluorescence, is present between the PD device 12 and the indicator layer 17. The light blocking layer 18, which has a predetermined thickness and covers the side surface of the indicator layer, serves to transmit the analyte.

As shown in FIG. 11, the fluorescence sensor 10C further includes a protective layer 19 made of polyimide, parylene, cyclic polyolefine, or any other suitable resin. The fluorescence sensor 10C measures the analyte 2 in a body fluid or the blood in a subject after the subject punctures his/her body with a distal end portion of the protective layer 19, that is, the portion on the side where the light blocking layer 18 is present. The material of the protective layer 19 contains carbon black or any other suitable light blocking material and is hence optically opaque so that external light is blocked. The silicon substrate 11, the PD device 12, the silicon oxide film 13, and the filter 14 are the same as those in the fluorescence sensor 10 of the first embodiment and other fluorescence sensors. The light blocking layer 18 is formed on the filter 14 on the distal end side, and the indicator layer 17 is formed on the filter 14 on the proximal end side. The LED device 15 is disposed on the indicator layer 17. That is, in the fluorescence sensor 10C, the PD device 12, which is a photoelectric conversion device, the filter 14, the indicator layer 17, and the LED device 15, which is a light emitting device, are formed in this order above the first principal surface of the silicon substrate 11, which is a base member.

Further, in the fluorescence sensor 10C, a long wavelength cutoff filter 14D is disposed between the LED device 15, which is a light emitting device, and the indicator layer 17. The long wavelength cutoff filter 14D serves to block light having a wavelength longer than that of excitation light.

In the fluorescence sensor 10C, the indicator layer 17 is irradiated with the excitation light which is emitted from the LED device 15 and from which long wavelength light components are cut off by the long wavelength cutoff filter 14D. The fluorescence from the indicator layer 17 passes through the filter 14 and the silicon oxide film 13 and is detected by the PD device 12.

The fluorescence sensor 10C of the present embodiment not only has the advantageous effect provided by the fluorescence sensor 10A of the first embodiment but also includes the long wavelength cutoff filter 14D, which prevents light having a wavelength longer than that of the excitation light, even if emitted from the light emitting device, from being incident on the PD device 12. As a result, the PD device 12 detects only fluorescence, whereby the signal-to-noise ratio of a detected signal is improved.

Fifth Embodiment

A fluorescence sensor 10D according to a fifth embodiment of the present invention will be described. The fluorescence sensor 10D of the present embodiment is similar to the fluorescence sensor 10 of the first embodiment and other fluorescence sensors. The same components therefore have the same reference characters and no description thereof will be made.

In the fluorescence sensor 10 of the first embodiment, the disposed filter 14 cuts off unwanted excitation light originating from the light emitting device and impinging on the PD device 12. In contrast, the fluorescence sensor 10D of the present embodiment includes a structurally characteristic PD device 12D, whereby no unwanted excitation light is detected even without the filter 14. The basic structure of the fluorescence sensor 10D of the fifth embodiment is the same as those of the fluorescence sensor 10 of the first embodiment and other fluorescence sensors except that no filter 14 is present.

Figure 12A:
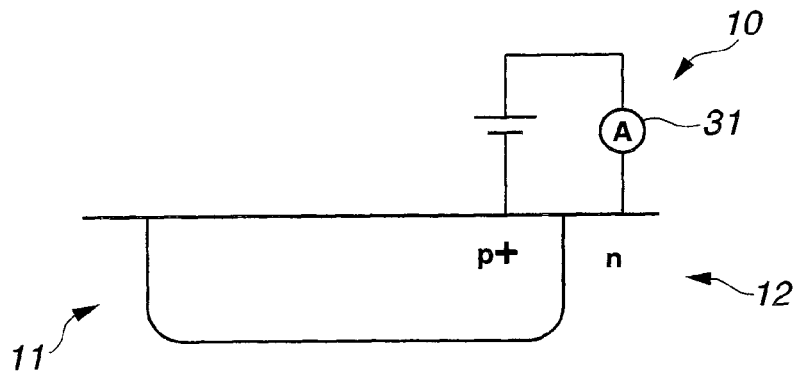
FIG. 12A is a cross-sectional diagrammatic view for describing a photodiode device in the fluorescence sensor according to the first embodiment.
Figure 12B:
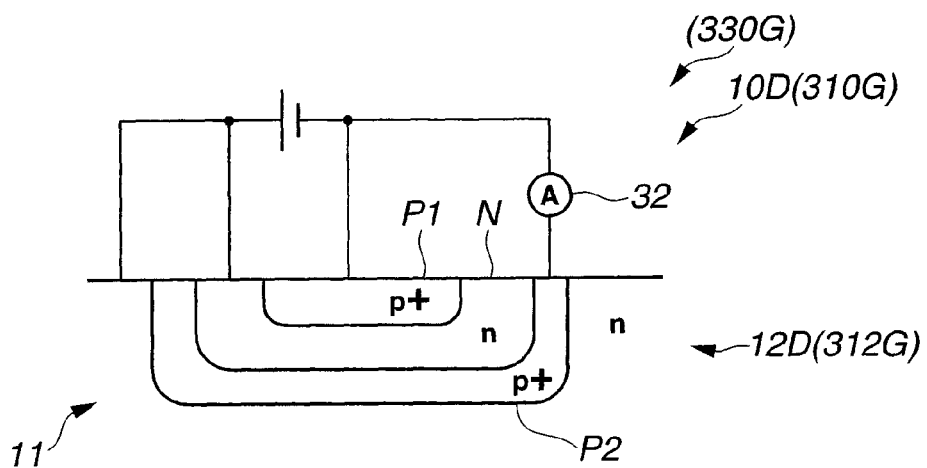
FIG. 12B is a cross-sectional diagrammatic view for describing a photodiode device in a fluorescence sensor according to a fifth embodiment.
Figure 12C:
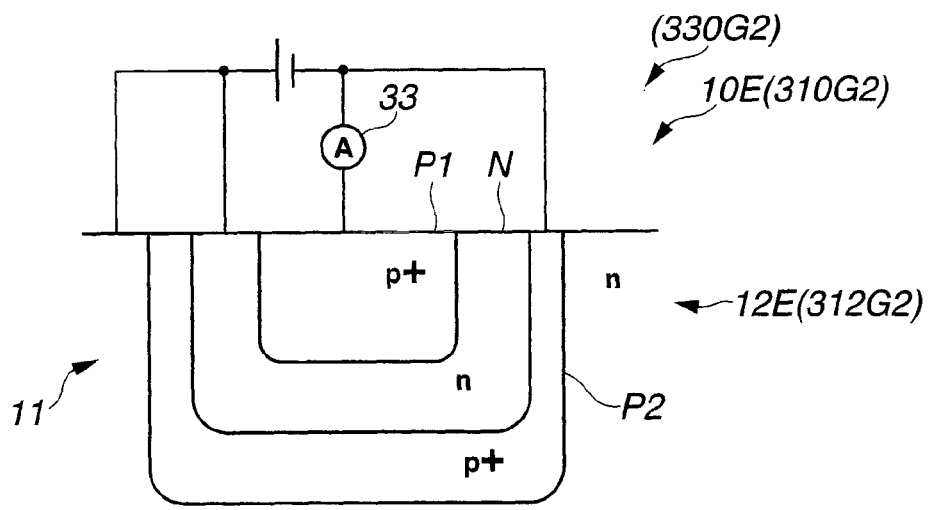
FIG. 12C is a cross-sectional diagrammatic view for describing a photodiode device in a fluorescence sensor according to a variation of the fifth embodiment.

FIGS. 12A to 12C are diagrammatic cross-sectional views of the structure of the PD device in the fluorescence sensor. In the PD device 12 in the fluorescence sensor 10 of the first embodiment and other fluorescence sensors shown in FIG. 12A, an ammeter 31 detects a fluorescence signal in the form of current flowing between an n region and a p+ region. In contrast, in the fluorescence sensor 10D of the present embodiment shown in FIG. 12B, the PD device 12D includes two PD light receiving portions (p+ regions) P1 and P2, which are formed in the silicon substrate 11 but at different depth levels, and an ammeter 32 detects the current flowing through the PD light receiving portion P2 formed at the deeper level. As a result, the PD device 12D can produce a fluorescence signal from which the influence of the light penetrating to shallower depths, that is, the influence of light components having shorter wavelengths, is electrically removed.

As a result, the fluorescence sensor 10D of the present embodiment, which has a simple structure with no filter 14, can provide the same advantageous effect as that provided by the fluorescence sensor 10 of the first embodiment.

As described above, the PD device 12D in the fluorescence sensor 10D of the present embodiment includes the first light receiving portion P1 and the second light receiving portion P2 formed at a deeper level than the level where the first light receiving portion P1 is formed with an n region N interposed between the first light receiving portion P1 and the second light receiving portion P2, to which the same bias voltage is applied. The PD device 12D detects the current flowing through the second light receiving portion P2 so that an electric signal representing the incident excitation light is electrically cut off.

The same filter as that used in the fluorescence sensor 10 of the first embodiment and other fluorescence sensors, which absorbs excitation light but transmits fluorescence, may further be disposed in the fluorescence sensor 10D. The above description has been made with reference to the case where each of the light receiving portions is formed of a P-type diode, but the conductivity and the polarity of the light receiving portions may be reversed. That is, each of the light receiving portions may be formed of an N-type diode.

Variation of Fifth Embodiment

A fluorescence sensor 10E according to a variation of the fifth embodiment of the present invention will be described. The fluorescence sensor 10E of the present embodiment is similar to the fluorescence sensor 10D of the fifth embodiment. The same components therefore have the same reference characters and no description thereof will be made.

Since the fluorescence sensor 10D of the fifth embodiment includes the structurally characteristic PD device 12D, no unwanted excitation light is detected even without the filter 14. In contrast, the fluorescence sensor 10E of the present variation includes the filter 14 that cuts off the excitation light and a structurally characteristic PD device 12E, as in the fluorescence sensor 10D.

That is, the PD device 12E in the fluorescence sensor 10E includes two PD light receiving portions (p+ regions) P1 and P2 formed in the silicon substrate 11 but at different depth levels, and an ammeter 33 detects the current flowing through the PD light receiving portion P1 formed at the shallower level, as shown in FIG. 12C.

The fluorescence sensor 10E provides the same advantageous effect as those provided by the fluorescence sensor 10D and other fluorescence sensors and can detect a fluorescence signal that further excels in signal-to-noise ratio.

As described above, in the fluorescence sensor 10E of the present embodiment, the PD device 12E includes the first light receiving portion P1 and the second light receiving portion P2 formed at a deeper level than the level where the first light receiving portion P1 is formed with an n region N interposed between the first light receiving portion P1 and the second light receiving portion P2, to which the same bias voltage is applied. The PD device 12E detects the current flowing through the first light receiving portion P1 so that an electric signal representing noise light having a wavelength longer than that of fluorescence is electrically cut off.

It is also possible in the fluorescence sensor 10D or the fluorescence sensor 10E to produce a fluorescence signal having an optimum signal-to-noise ratio by applying different reverse bias voltages to the two PD light receiving portions shown in FIG. 12B or 12C to adjust the applied bias voltages.

Sixth Embodiment

Figure 13:
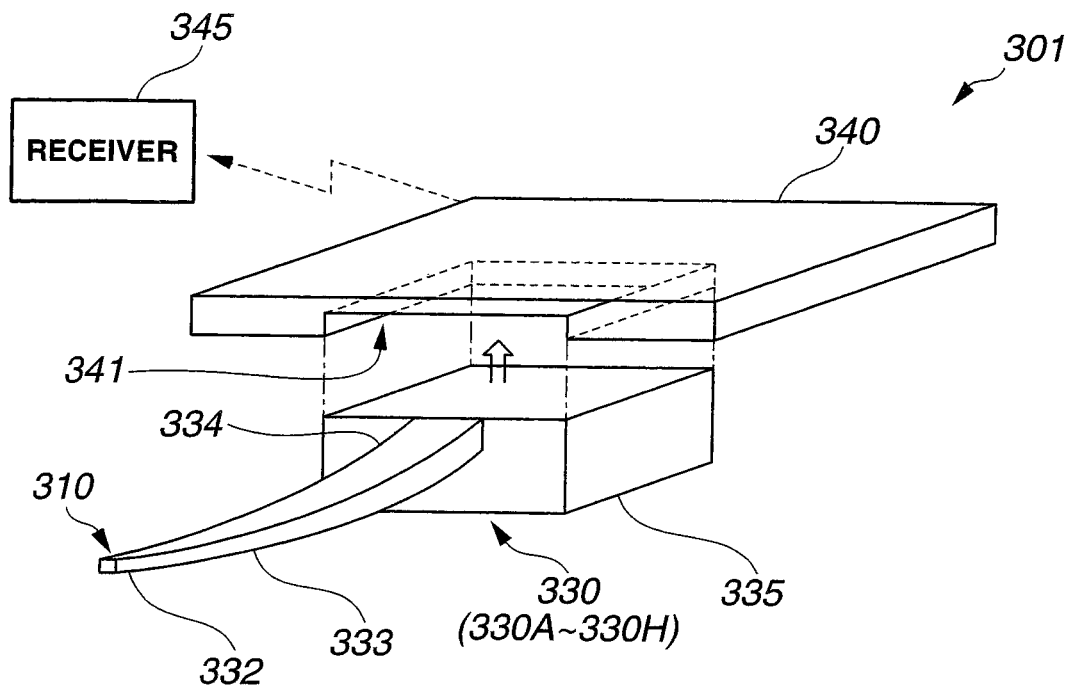
FIG. 13 is a diagrammatic view of a sensor system including a needle-type fluorescence sensor according to a sixth embodiment.

A needle-type fluorescence sensor 330 according to a sixth embodiment of the present invention will be described below with reference to the corresponding drawings. As shown in FIG. 13, the needle-type fluorescence sensor 330 of the present embodiment is combined with a body unit 340 and a receiver 345 and used as a sensor system 301. That is, the sensor system 301 includes the needle-type fluorescence sensor 330, the body unit 340, which sends information measured by the needle-type fluorescence sensor 330, and the receiver 345, which receives and stores a signal from the body unit 340. The signal communication between the body unit 340 and the receiver 345 is carried out in a wireless or wired manner.

The needle-type fluorescence sensor 330 includes an elongated needle body section 333 having a sensor portion 310, which is the fluorescence sensor of the first embodiment and disposed at a needle distal end portion 332, and a connector 335 integrated with a needle proximal end portion 334 of the needle body section 333. The connector 335 detachably fits into a fitting portion 341 of the body unit 340. The needle-type fluorescence sensor 330 is electrically connected to the body unit 340 when the connector 335 mechanically fits into the fitting portion 341 of the body unit 340. The needle body section 333 may be tapered in such a way that the needle distal end portion has a cross-sectional area smaller than that of a needle central portion so that the needle distal end portion can punctures a subject, whereas the needle proximal end portion 334 of the needle body section 333 may have a cross-sectional area larger than that of the needle central portion. To reduce burden on the subject, the cross-sectional dimension of the tip of the needle body section 333 is preferably 200 by 200 μm or smaller.

As will be described later, the needle body section 333 and the connector 335 can be formed by using etching and/or machining monolithically from a silicon substrate on which the sensor portion 310, metal wiring, and other components are formed.

The body unit 340 includes, although not shown, a wireless antenna for sending and receiving a signal wirelessly to and from the receiver 345, a battery or any other suitable power source, and a variety of circuits for driving and controlling the sensor portion 310. Examples of the variety of circuits may include an amplification circuit that amplifies a signal, a circuit-reference-clock generation circuit, a logic circuit, a data processing circuit, an AD conversion process circuit, a mode control circuit, a memory circuit, and a radio-frequency communication wave generation circuit. When a signal is sent and received to and from the receiver 345 in a wired manner, the body unit 340 includes a signal line instead of the wireless antenna.

The needle-type fluorescence sensor 330 is a disposable unit that is to be discarded after use to prevent infection and other accidents, whereas the body unit 340 and the receiver 345 are reused units that are to be repeatedly reused.

A subject himself/herself punctures his/her body surface with the needle body section 333 of the needle-type fluorescence sensor 330 that fits into the body unit 340, and the needle distal end portion 332 indwells under the dermal layer in the body. Alternatively, after the subject himself/herself punctures his/her body surface with the needle body section 333, the subject may fit the needle-type fluorescence sensor 330 into the body unit 340. The sensor system 301 can continuously measure, for example, the concentration of glucose in a body fluid and store the measurements in a memory in the receiver 345. That is, the needle-type fluorescence sensor 330 of the present embodiment is a short-term subcutaneous indwelling, needle-type fluorescence sensor, which means that the needle-type fluorescence sensor 330 is continuously used for approximately a week. In particular, the needle-type fluorescence sensor 330 can be preferably used as a glucose continuous monitoring apparatus.

The structures of the needle body section 333 and the sensor portion 310 disposed in the needle distal end portion 332 of the needle-type fluorescence sensor 330 will be described with reference to FIGS. 14 and 15.

Figure 14:
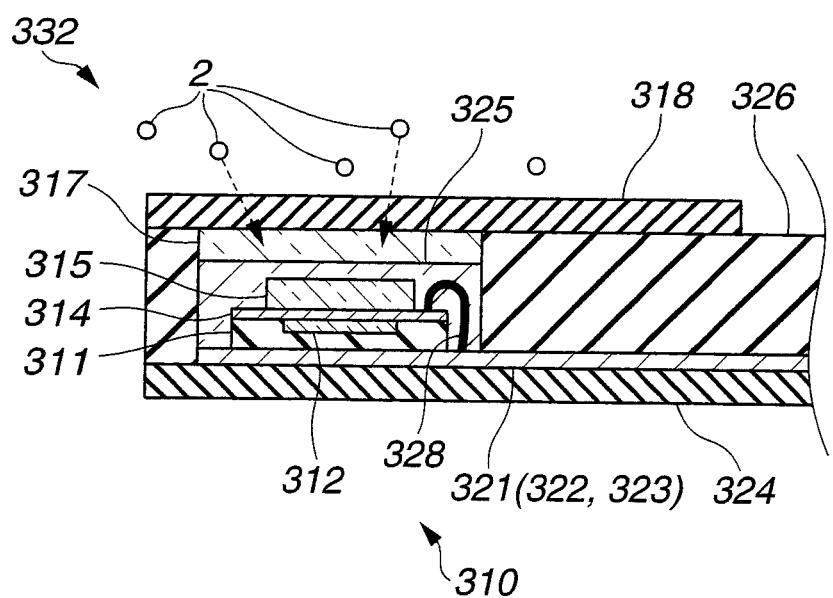
FIG. 14 is a cross-sectional diagrammatic view for describing a cross-sectional structure of a needle distal end portion of the needle-type fluorescence sensor according to the sixth embodiment.

As shown in FIG. 14, the needle body section 333 of the needle-type fluorescence sensor 330 includes a resin substrate 324, a protective layer 326, and six metal lines 321, 322, and 323.

The resin substrate 324 and the protective layer 326 are made of polyimide, poly-para-xylene, cyclic polyolefine, or any other suitable resin, and the materials thereof contain carbon black or any other suitable light blocking material and are hence optically opaque in order to block external light from entering the needle distal end portion 332.

The metal lines 321, 322, and 323 are made of aluminum, copper, or any other suitable conductor, and not only serve as electric wiring in the sensor portion 310 but also have a function of increasing the rigidity of the needle body section 333. The metal lines 321, 322, and 323 are disposed from the sensor portion 310 disposed in the needle distal end portion 332 to the needle proximal end portion 334, further extend to the connector 335, and are connected to the variety of circuits in the body unit, which fits into the connector 335.

The metal line 321 transfers a fluorescence signal from a photodiode (hereinafter also referred to as "PD") device 312, which is a photoelectric conversion device, to the body unit 340. The metal line 322 supplies driving electric power from the body unit 340 to a light emitting diode (hereinafter also referred to as "LED") device 315, which is a light emitting device. The metal line 323 transfers a temperature signal from a temperature sensor 327 (see FIG. 15) to the body unit 340.

Figure 15:
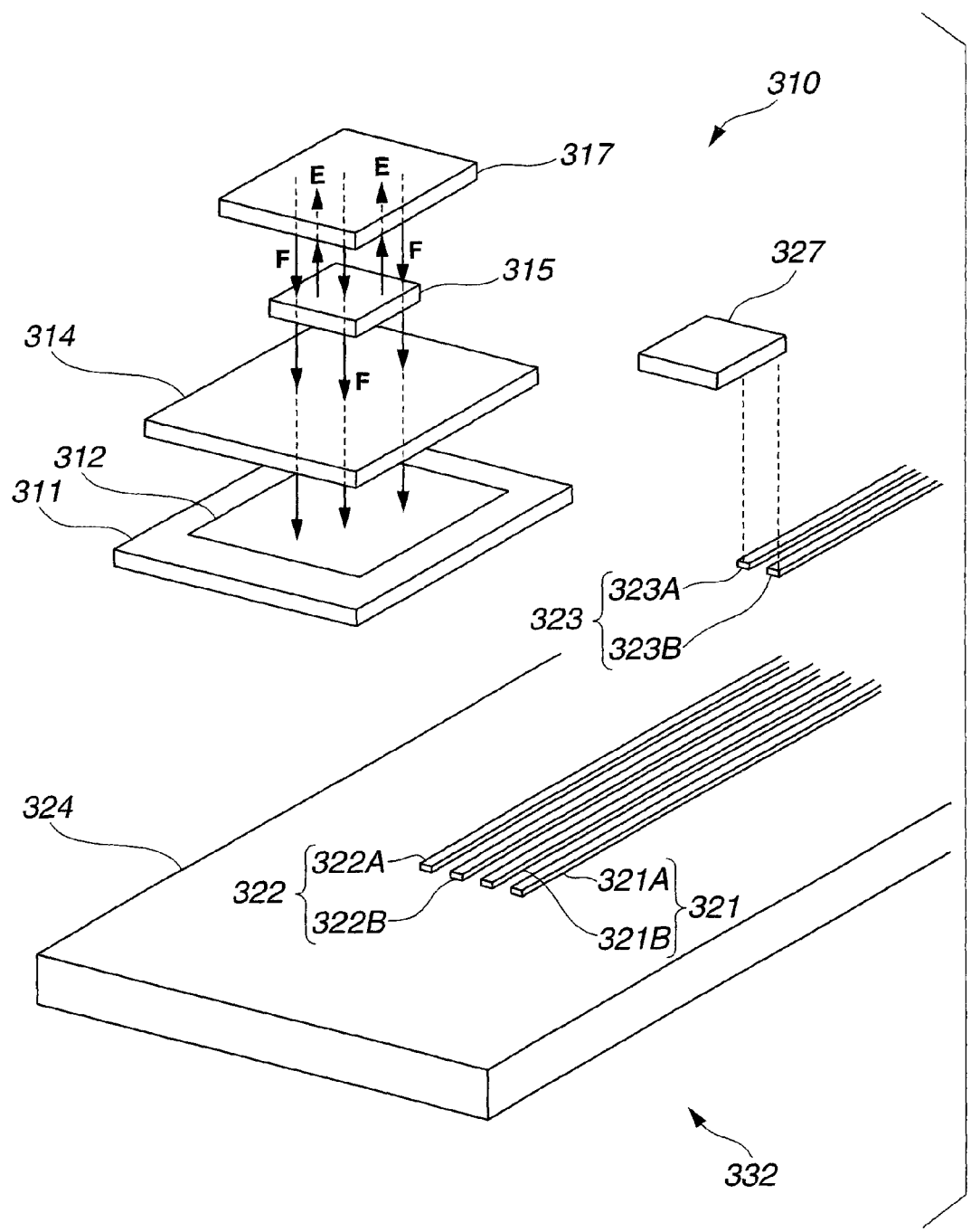
FIG. 15 is an exploded view for describing the structure of the needle distal end portion of the needle-type fluorescence sensor according to the sixth embodiment.

FIG. 15 illustrates a case where each of the metal lines 321, 322, and 323 is formed of two metal lines: the metal line 321 is formed of metal lines 321A and 321B; the metal line 322 is formed of metal lines 322A and 322B; and the metal line 323 is formed of metal lines 323A and 323B, and the metal lines 321, 322, the metal line 323, and an insulating layer (not shown) interposed therebetween form a multilayer structure. The material of the insulating layer may be the same material as that of the protective layer 326. In this case, the metal lines 321, 322, and 323 are buried in the protective layer 326. The metal lines 321, 322, and 323 shown in FIG. 15 are located under a silicon substrate 311, but may be formed on the silicon substrate 311.

The metal lines 321, 322, and 323 can be formed by an additive method, such as deposition, sputtering, plating, and a combination of any of the methods described above; a subtractive method in which a metal foil is etched; or using bulk thin lines.

The basic structure of the sensor portion 310 is that of the fluorescence sensor 10 described above, but the reference characters of the components are expressed by the numbers used for the fluorescence sensor 10 to which 300 is added. That is, the needle-type fluorescence sensor 330 includes the fluorescence sensor 10.

The PD device 312 is electrically connected to the metal line 321 via a bonding wire 328, through-wiring, or any other suitable means.

A light blocking layer 318 made of a hydrogel, carbon black, and other materials is formed on an indicator layer 317, that is, as a top surface of the sensor portion, and blocks various kinds of light. The light blocking layer 318 serves to transmit an analyte. Each of the indicator layer 317 and the light blocking layer 318 is set at approximately several tens of micrometers in thickness. The light blocking layer 318 may cover the entire needle-type fluorescence sensor 330 as well as the needle distal end portion 332, or only the needle distal end portion 332. In the latter case, the portions other that the needle distal end portion 332 may be covered with a different member, such as a metal film made of titanium, for the light blocking purpose. The needle-type fluorescence sensor 330 including the light blocking layer 318 is safe for human bodies because no excitation light leaks outward and can produce a fluorescence signal having a satisfactory signal-to-noise ratio.

As shown in FIG. 15, the temperature sensor 327 is also disposed in the sensor portion 310 of the needle distal end portion 332. A temperature signal from the temperature sensor 327 is transferred to the body unit 340 through the metal line 323. Examples of the temperature sensor 327 include a fluorescence thermometer or any other optical temperature sensor, a thermistor-type temperature sensor, a thin metal film resister-type temperature sensor, and a semiconductor temperature sensor based on temperature characteristics of the forward current flowing through a PN junction. A semiconductor temperature sensor is preferred from the viewpoint of good linearity of the response to temperature and easiness of the formation of the temperature sensor on the silicon substrate 311, which will be described later. That is, although the temperature sensor 327 is separate from the silicon substrate 311 in FIG. 15, a semiconductor temperature sensor 327 can alternatively be formed on the silicon substrate 311 on which the PD device 312 is formed.

In a needle-type fluorescence sensor including the PD device 312 as a photoelectric conversion device, the PD device 312 can also be used as the temperature sensor. That is, the PD device 312 can be used as the temperature sensor when no photoelectric conversion operation is carried out.

As described above, the needle-type fluorescence sensor of the present embodiment has the fluorescence sensor of the first embodiment, and includes the needle body section including the sensor portion, which is the fluorescence sensor disposed in the needle distal end portion that indwells in a living body, and a plurality of metal lines disposed from the sensor portion to the needle proximal end portion; and the connector, which is integrated with the needle body section and in which the plurality of metal lines extend.

The operation of the needle-type fluorescence sensor 330 will be described. As already described, to use the needle-type fluorescence sensor 330, a subject punctures his/her body surface and the dermal layer under the skin with the needle distal end portion 332 and part of the needle body section 333, inserts them, and keeps them indwelling there. To insert the needle-type fluorescence sensor 330 into the body, the subject may use an outer needle or any other suitable component as required. The needle-type fluorescence sensor 330 may be inserted into a suitable tissue in a living body, for example, a blood vessel, in accordance with the purpose and kept indwelling there. When blood or any other body fluid circulates through a tube or any other similar component connecting a living body and a component external thereto, the subject may puncture the tube external to the living body with the needle-type fluorescence sensor 330. The fluorescence sensor inserted and kept indwelling in the dermal layer responds to an analyte and detects it in a particularly satisfactory manner.

First, the LED device 315 emits excitation light when the body unit 340 supplies a driving electric power signal through the connector 335 and the metal line 322 in the needle body section 333. The pulse width of the light emitted from the LED device 315 ranges from 10 to 100 ms. The magnitude of pulse current ranges from approximately 1 to 100 mA. The central wavelength of the excitation light is approximately 375 nm. The excitation light is emitted, for example, every 30 seconds.

The excitation light from the LED device 315 enters the indicator layer 317. The indicator layer 317 produces fluorescence whose intensity is proportional to the amount of analyte 2. The analyte 2 passes through the light blocking layer 318 and enters the indicator layer 317. The fluorescent dye in the indicator layer 317 emits fluorescence, for example, having a wavelength of 460 nm in response to the excitation light having a wavelength of 375 nm.

The fluorescence from the indicator layer 317 passes through the LED device 315, a filter 314, and other components and impinges on the PD device 312. That is, the LED device 315 in the needle-type fluorescence sensor 330 transmits fluorescence. The fluorescence then undergoes photoelectric conversion in the PD device 312 and light-induced electric charge or a fluorescence signal is produced, which is transferred through the metal line 321 to the body unit 340.

In the needle-type fluorescence sensor 330, an amplification circuit IC can be disposed in the vicinity of the PD device 312. In this case, a fluorescence signal from the PD device 312 is amplified and then transferred through the metal line 321 to the body unit 340, whereby the signal can have a more satisfactory signal-to-noise ratio.

A temperature signal from the temperature sensor 327 is also transferred to the body unit 340 through the metal line 323, like a fluorescence signal from the PD device 312.

The data on the fluorescence intensity measured by the needle-type fluorescence sensor 330 is transferred as digital data information expressed, for example, in 12 bits or higher through the wireless antenna on the body unit 340 to the receiver 345 approximately every 10 minutes. The fluorescence intensity data is corrected based on the temperature and other information. The concentration of the analyte is thus calculated.

The receiver 345 stores the calculated concentration of the analyte in a memory. At the same time, the concentration of the analyte may be displayed on a display unit and an alert may be issued when the concentration of the analyte exceeds a preset range.

When the operation mode of the needle-type fluorescence sensor 330 can be selected from, for example, a sleep mode, an on/off mode, and a safety mode, the life of the battery or any other power source that drives the sensor portion 310 can be prolonged by selecting an appropriate mode.

The needle-type fluorescence sensor 330 can freely change the length of the needle body section 333, that is, can increase the length as required, whereby other various types of sensor, such as a pH sensor and an insulin sensor, can be disposed next to the sensor portion 310.

As described above, since the sensor portion 310 of the needle-type fluorescence sensor 330 of the present embodiment electrically transfers communication and other signals through the metal lines 321, 322, and 323, no optical fiber is required. As a result, the needle-type fluorescence sensor 330 produces a stable sensor signal even when the needle body section 333 is deformed. Further, the needle-type fluorescence sensor 330 can be readily fabricated and the size thereof can be reduced at the same time because no optical fiber is used. Moreover, since a fluorescence signal is converted into an electric signal in the needle distal end portion 332, the needle-type fluorescence sensor 330 is more sensitive than an optical fiber sensor. That is, the needle-type fluorescence sensor 330 is a highly sensitive, highly precise, small, inexpensive, stable needle-type fluorescence sensor. Further, the resin substrate 324, the metal lines 321, 322, and 323, and the protective layer 326 disposed in the needle body section 333 of the needle-type fluorescence sensor 330 provide high flexibility and strength.

Further, the needle-type fluorescence sensor 330 is a small, precise analyte detection fluorescence sensor that readily allows the distal end portion to be reduced in size and hence to be inserted through a dermal layer. Moreover, in the needle-type fluorescence sensor 330, degradation in signal quality is significantly reduced even when, for example, the needle body section is bent. As described above, the needle-type fluorescence sensor 330 has a simple configuration and high detection sensitivity.

Being suitable for long-term continuous measurement, the needle-type fluorescence sensor 330 can in particular be preferably used as a short-term subcutaneous indwelling, needle-type glucose sensor for quantifying a saccharide in blood.

Seventh Embodiment

A needle-type fluorescence sensor 330A according to a seventh embodiment of the present invention will be described with reference to FIGS. 16A and 16B. The needle-type fluorescence sensor 330A of the present embodiment is similar to the needle-type fluorescence sensor 330 of the sixth embodiment. The same components therefore have the same reference characters and no description thereof will be made.

Figure 16A:
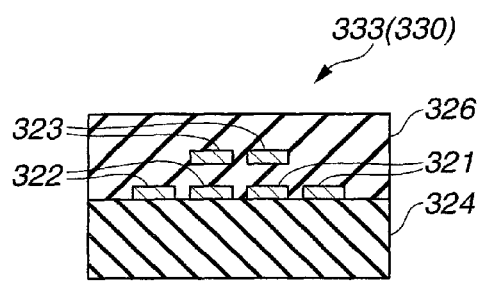
FIG. 16A is a cross-sectional diagrammatic view for describing the structure of a needle body section of the needle-type fluorescence sensor according to the sixth embodiment.
Figure 16B:
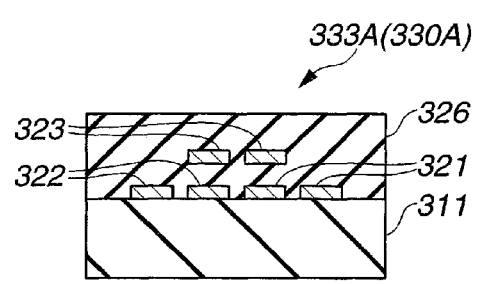
FIG. 16B is a cross-sectional diagrammatic view for describing the structure of a needle body section of a needle-type fluorescence sensor according to a seventh embodiment.

As shown in FIG. 16A, the needle body section 333 of the needle-type fluorescence sensor 330 of the sixth embodiment includes the resin substrate 324, the metal lines 321, 322, and 323, and the protective layer 326. In contrast, a needle body section 333A of the needle-type fluorescence sensor 330A of the present embodiment includes the silicon substrate 311, the metal lines 321, 322, and 323, and the protective layer 326, as shown in FIG. 16B. That is, instead of the resin substrate 324 in the needle body section 333 of the needle-type fluorescence sensor 330 of the sixth embodiment, the needle body section 333A of the needle-type fluorescence sensor 330A of the present embodiment includes the silicon substrate 311.

The silicon substrate in the needle body section 333A is an extension of the silicon substrate 311 on which the PD device 312 is formed. As already described above, since the silicon substrate 311 is reduced in thickness to approximately several tens of micrometers, the needle body section 333A shows flexibility. To redeem the brittleness of the silicon substrate 311 and reinforce it, titanium, SUS, or any other suitable metal material may be formed on the backside of the silicon substrate 311.

In addition to the advantageous effect provided by the needle-type fluorescence sensor 330 of the sixth embodiment including the resin substrate 324, the needle body section 333A of the needle-type fluorescence sensor 330A of the present embodiment not only further excels the needle body section 333 in strength characteristics but also shows flexibility. Since the needle body section 333A has rigidity, the needle-type fluorescence sensor 330A is readily inserted through a body surface. As a result, the needle-type fluorescence sensor 330A can be inserted without any outer needle but only by using the needle body section 333A.

It is further preferred that the structure that primarily forms the connector 335 be also monolithically formed from the silicon substrate 311. The needle-type fluorescence sensor 330 including the sensor portion (needle distal end portion) having a fluorescence sensor, the needle body section 333A, and the connector 335, each of which is monolithically formed from the silicon substrate 311, provides the advantageous effect provided by the needle-type fluorescence sensor 330A and allows the manufacturing steps to be further simplified.

That is, a needle-type fluorescence sensor for continuously measuring a saccharide in a living body includes: a sensor potion disposed in a needle distal end portion and penetrating a living body and indwelling there; a needle body section in which a plurality of metal lines are disposed from the sensor portion to a needle proximal end portion; and a connector in which the plurality of metal lines extend and which detachably fits into a body unit that sends information detected by the sensor portion to a receiver, the sensor portion, the needle body section, and the connector monolithically formed from a silicon substrate having first and second principal surfaces. The sensor portion includes an excitation light emitting device made of a gallium nitride-based compound semiconductor and formed on a sapphire substrate, an indicator layer that produces fluorescence according to the concentration of the saccharide when interacting with the saccharide in the blood or a body fluid under the excitation light, a photoelectric conversion device formed of a photodiode or a phototransistor that converts the fluorescence into an electric signal, a filter that reflects and/or absorbs the excitation light having a wavelength shorter than that of the fluorescence but transmits the fluorescence, and a light blocking layer 318 capable of transmitting the saccharide. The filter, the light emitting device, the indicator layer, and the light blocking layer 318 overlap with each other in this order above the photoelectric conversion device formed on the first principal surface of the silicon substrate. The fluorescence produced in the indicator layer passes through the light emitting device and is converted into the electric signal in the photoelectric conversion device.

Eighth Embodiment

A needle-type fluorescence sensor 330B according to an eighth embodiment of the present invention will be described with reference to FIGS. 17A and 17B. The needle-type fluorescence sensor 330B of the present embodiment is similar to the needle-type fluorescence sensor 330 of the sixth embodiment. The same components therefore have the same reference characters and no description thereof will be made.

Figure 17A:
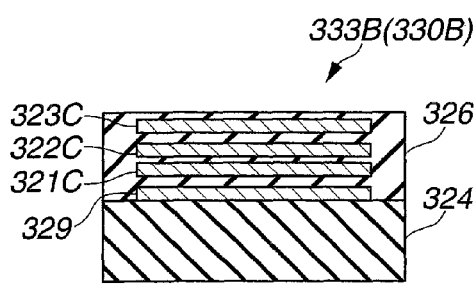
FIG. 17A is a cross-sectional diagrammatic view for describing the structure of a needle body section of a needle-type fluorescence sensor according to an eighth embodiment.

As shown in FIG. 17A, a needle body section 333B of the needle-type fluorescence sensor 330B includes four metal lines 321C, 322C, 323C, and 329. The metal line 321C transfers a fluorescence signal from the PD device 312 to the body unit 340. The metal line 322C supplies driving electric power from the body unit 340 to the LED device 315. The metal line 323C transfers a temperature signal from the temperature sensor 327 to the body unit 340. The metal line 329 is a common ground line. That is, in the needle-type fluorescence sensor 330B, the number of metal lines inserted through the needle body section 333B can be reduced by sharing a single ground line among various members in the sensor portion. For example, signals can be sent and received to and from the sensor portion 310 only with four metal lines.

Further, in a needle-type fluorescence sensor in which the PD device 312 is used as the temperature sensor, signals can be sent and received to and from the sensor portion 310 only with, for example, three metal lines.

In addition to the advantageous effect provided by the needle-type fluorescence sensor 330, the needle-type fluorescence sensor 330B of the present embodiment allows the number of metal lines to be reduced, whereby the needle body section 333B can be reduced in terms of cross-sectional area, that is, in terms of diameter. The needle body section 333B can be reduced in diameter also because the needle-type fluorescence sensor 330B has metal lines formed in a multilayer structure.

FIG. 17A shows a form similar to that of the needle-type fluorescence sensor 330 of the sixth embodiment but different therefrom in that the needle body section 333B does not have the silicon substrate 311. The silicon substrate may alternatively be left, as in the needle-type fluorescence sensor 330A of the seventh embodiment. That is, the configuration of the metal lines in the needle-type fluorescence sensor 330B of the eighth embodiment can be used not only in the needle-type fluorescence sensor 330A of the seventh embodiment but also in the needle-type fluorescence sensor 330 of the sixth embodiment.

Figure 17B:
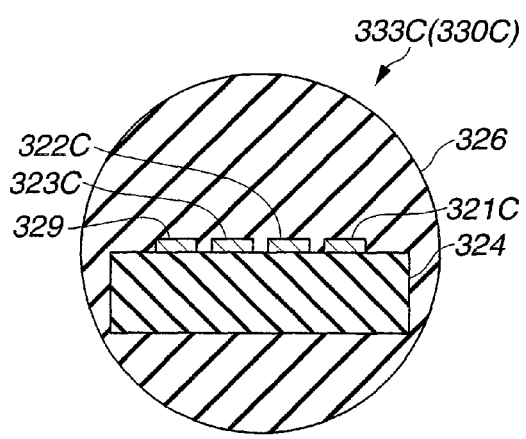
FIG. 17B is a cross-sectional diagrammatic view for describing the structure of the needle body section of the needle-type fluorescence sensor according to the eighth embodiment.

It is also, of course, possible to employ a structure in which the metal lines 321C, 322C, 323C, and 329 in a needle body section 333C are not formed in a multilayer wiring structure, as indicated by a needle-type fluorescence sensor 330C in FIG. 17B. Further, the cross-sectional shape of the needle body section 333C is not necessarily rectangular but may be, for example, circular, as indicated by the needle-type fluorescence sensor 330C.

Ninth Embodiment

A needle-type fluorescence sensor 330D according to a ninth embodiment of the present invention will be described. The needle-type fluorescence sensor 330D of the present embodiment is similar to the needle-type fluorescence sensor 330 of the sixth embodiment. The same components therefore have the same reference characters and no description thereof will be made.

Figure 18:
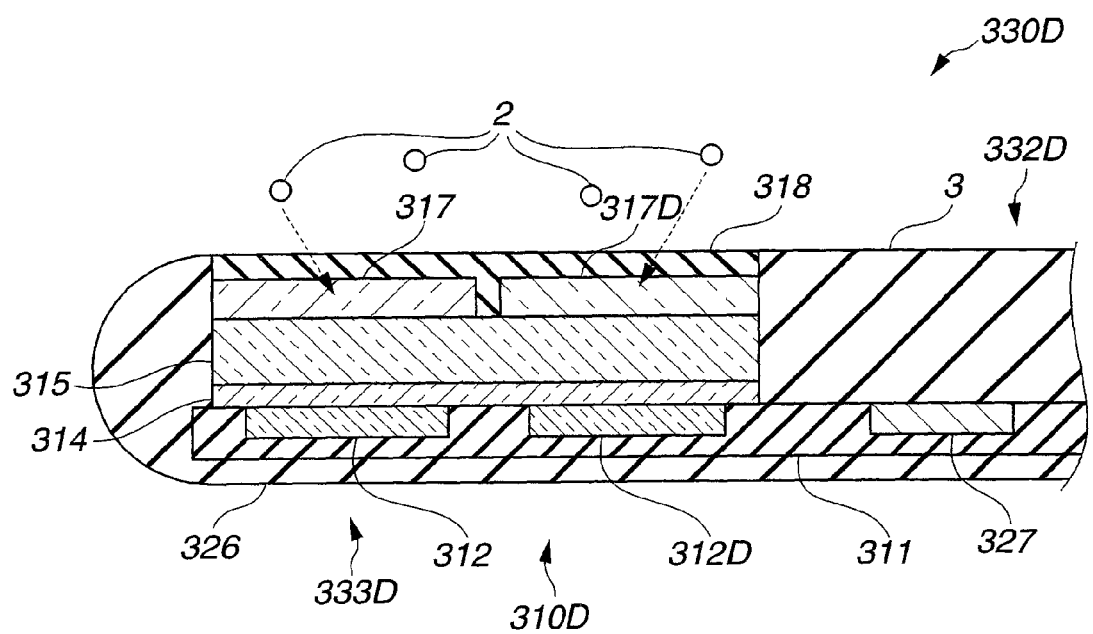
FIG. 18 is a cross-sectional diagrammatic view for describing a cross-sectional structure of a needle distal end portion of a needle-type fluorescence sensor according to a ninth embodiment.

As shown in FIG. 18, a sensor portion 310D of the needle-type fluorescence sensor 330D includes not only the PD device 312, which is a first photoelectric conversion device, provided in the sensor portion 310 of the needle-type fluorescence sensor 330 and other needle-type fluorescence sensors (hereinafter referred to as "first PD device") but also a second PD device 312D having the same function as that of the first PD device 312 and a comparison indicator layer 317D. The comparison indicator layer 317D is made of a hydrogel or any other suitable material, like the indicator layer 317, but contains no fluorescent dye. The comparison indicator layer 317D therefore emits fluorescence produced in the hydrogel or other materials when excitation light is incident, that is, fluorescence produced in a state in which no analyte 2 is present. That is, the second PD device 312D provided in the sensor portion 310D outputs an offset signal, which is an electric signal that is not affected by any analyte.

FIG. 18 shows an exemplary configuration in which the first PD device 312, the second PD device 312D, the temperature sensor 327, and the filter 314 are integrally formed on the surface of the silicon substrate 311 in a semiconductor manufacturing step, but does not show any metal wiring. As shown in FIG. 18, the LED device 315, the filter 314, and the light blocking layer 318 are shared by the first PD device 312 and the second PD device 312D.

In the needle-type fluorescence sensor 330D, when the LED device 315 irradiates the indicator layer 317 and the comparison indicator layer 317D with excitation light, the first PD device 312 outputs a fluorescence signal corresponding to the concentration of the analyte in the indicator layer 317, and the second PD device 312D outputs an offset signal, which is an electric signal from the comparison indicator layer 317D produced when no analyte is present. In the needle-type fluorescence sensor 330D, an accurate fluorescence signal corresponding only to the concentration of the analyte can be produced by calculating the difference between the two signals.

As described above, in the needle-type fluorescence sensor 330D, the needle distal end portion includes a second sensor portion having the PD device 312D, which is the second photoelectric conversion device that outputs an electric signal that is not affected by any analyte.

In addition to the advantageous effect provided by the needle-type fluorescence sensor 330 of the sixth embodiment, the needle-type fluorescence sensor 330D of the present embodiment provides excellent detection precision because an analyte concentration signal having a more satisfactory signal-to-noise ratio can be detected.

Figure 19:
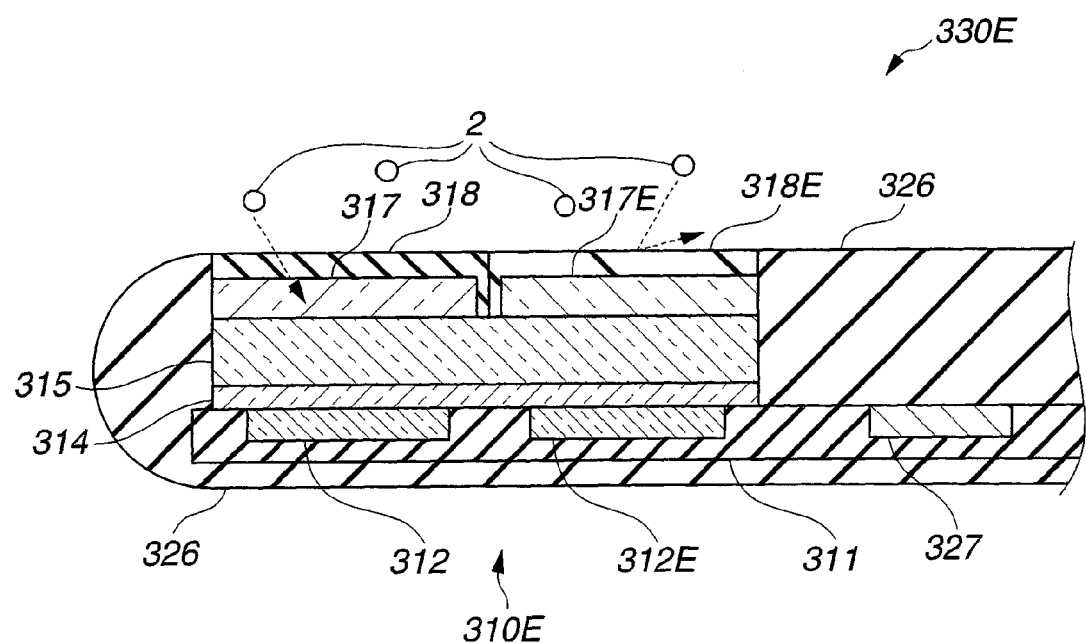
FIG. 19 is a cross-sectional diagrammatic view for describing a cross-sectional structure of a needle distal end portion of a needle-type fluorescence sensor according to a variation of the ninth embodiment.

FIG. 19 shows the structure of a needle-type fluorescence sensor 330E of a variation of the ninth embodiment, which provides the same advantageous effect as that provided by the needle-type fluorescence sensor 330D. That is, in the needle-type fluorescence sensor 330E, a comparison indicator layer 317E has the same configuration as that of the indicator layer 317 except that a light blocking layer 318E formed, for example, of a metal film is provided to prevent the analyte 2 from entering the comparison indicator layer 317E. When the analyte 2 includes a fluorescent dye that emits fluorescence under excitation light, it is preferable to use the needle-type fluorescence sensor 330E of the present variation.

Tenth Embodiment

A needle-type fluorescence sensor 330F according to a tenth embodiment of the present invention will be described. The needle-type fluorescence sensor 330F of the present embodiment is similar to the needle-type fluorescence sensor 330 of the sixth embodiment. The same components therefore have the same reference characters and no description thereof will be made.

In the needle-type fluorescence sensor 330 of the sixth embodiment and other needle-type fluorescence sensors, the light blocking layer 318 is disposed to allow the analyte 2 to enter the indicator layer 317 through the upper side thereof, as shown in FIG. 14 and other figures. In contrast, the basic structure of a sensor portion 310F of the needle-type fluorescence sensor 330F of the present embodiment is that of the fluorescence sensor 10C of the fourth embodiment, and the analyte 2 enters the indicator layer 317 via the light blocking layer 318 from the left when the fluorescence sensor 330F is viewed from the front, as shown in FIG. 20.

Figure 20:
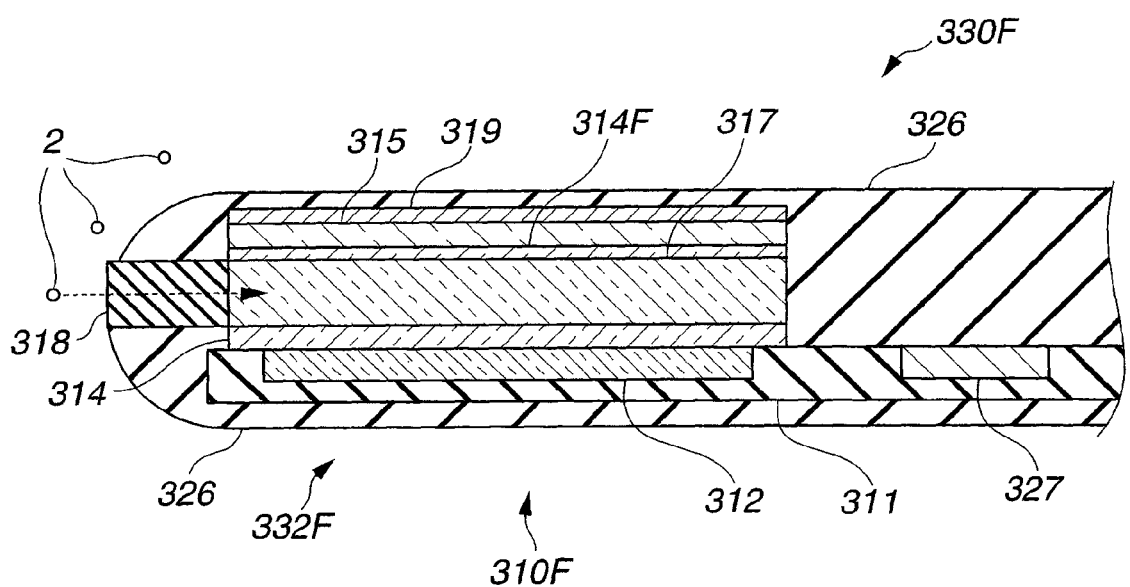
FIG. 20 is a cross-sectional diagrammatic view for describing a cross-sectional structure of a needle distal end portion of a needle-type fluorescence sensor according to a tenth embodiment.

That is, the sensor portion 310F of the needle-type fluorescence sensor 330F measures the analyte 2 in a body fluid in a subject after the subject punctures his/her body with the needle distal end portion 332, that is, the portion on the side where the light blocking layer 318 is present, as shown in FIG. 20. The needle body section 333 includes the protective layer 326, the silicon substrate 311, and the metal lines (not shown), and the protective layer 326 is made of a material containing carbon black or any other suitable light blocking material and hence optically opaque so that external light is blocked. The silicon substrate 311, the PD device 312, the filter 314, and other components are the same as those in the needle-type fluorescence sensor 330 of the sixth embodiment and other needle-type fluorescence sensors. The light blocking layer 318 is formed on the distal end side of the filter 314, and the indicator layer 317 is formed on the proximal end side thereof. The LED device 315 is disposed on the indicator layer 317, and a reflection layer 319 is formed on the LED device 315. That is, in the sensor portion 317F, the PD device 312, which is a photoelectric conversion device, the filter 314, the indicator layer 317, and the LED device 315, which is a light emitting device, are formed in this order above the first principal surface of the silicon substrate 311, which is a base member.

Further, in the sensor portion 310F, a long wavelength cutoff filter 314F having a function of blocking light having a wavelength longer than that of excitation light is disposed between the LED device 315, which is a light emitting device, and the indicator layer 317.

In the needle-type fluorescence sensor 330F, the excitation light emitted from the LED device 315, the light reflected off the reflection layer 319 and the light directly incident on the long wavelength cutoff filter 314F, passes through the filter 314F, where long wavelength components of the excitation light are cut off, and the resultant excitation light irradiates the indicator layer 317. The fluorescence from the indicator layer 317 passes through the filter 314 and is detected by the PD device 312.

In the needle-type fluorescence sensor 330F, the relationship between the indicator layer 317 and the light blocking layer 318 is not limited to the structure shown in FIG. 20. For example, although not shown, the light blocking layer 318 thick enough to reach the right side of the indicator layer 317 may be formed in part of the protective layer 326, or the light blocking layer 318 may have a tunnel-shaped structure passing through the protective layer 326. That is, in the needle-type fluorescence sensor shown in FIG. 20, the analyte 2 passes through the light blocking layer 318 and enters the indicator layer 317 from the right when the needle-type fluorescence sensor is viewed from the front. The structure described above may, of course, be combined with the structure shown in FIG. 20.

As described above, in the needle-type fluorescence sensor 330F, the indicator layer is formed above the photoelectric conversion device formed in the silicon substrate, and the light emitting device is disposed above the indicator layer with a filter therebetween. The light blocking layer 318 that covers a side surface of the indicator layer and has a predetermined thickness can transmit an analyte.

In the needle-type fluorescence sensor 330F of the present embodiment including the fluorescence sensor 10C, to detect fluorescence emitted from the analyte 2 having entered the indicator layer through the side surface thereof on the needle distal end side, the portions other than the distal end portion can be covered with the optically opaque protective layer 326. As a result, the needle-type fluorescence sensor 330F has no possibility of leakage of excitation light and is hence particularly safe in addition to the advantageous effect provided by the needle-type fluorescence sensor 330 and other needle-type fluorescence sensors.

Further, in the needle-type fluorescence sensor 330F, even when the LED device 315 emits light having a wavelength longer than that of the excitation light, the long wavelength cutoff filter 314F prevents the long-wavelength light from being incident on the PD device 312. As a result, the PD device 312 detects only fluorescence and hence produces a detected signal having a satisfactory signal-to-noise ratio. Further, the reflection layer 319 on the LED device 315 allows the emitted excitation light to irradiate the indicator layer 317 efficiently.

Eleventh Embodiment

A needle-type fluorescence sensor 330G according to an eleventh embodiment of the present invention will be described. The needle-type fluorescence sensor 330G of the present embodiment is similar to the needle-type fluorescence sensor 330 of the sixth embodiment. The same components therefore have the same reference characters and no description thereof will be made.

In the sensor portion 310 of the needle-type fluorescence sensor 330 of the sixth embodiment, the filter 314 is disposed to cut off unwanted excitation light originating from the LED device 315 and impinging on the PD device 312. In contrast, the basic structure of a sensor portion 310G of the needle-type fluorescence sensor 330G of the present embodiment is that of the fluorescence sensor 10D of the fifth embodiment shown in FIG. 12B. Since the sensor portion 310G includes two structurally characteristic PD devices 312G, no unwanted excitation light is detected even without the filter 314. The basic structure of the needle-type fluorescence sensor 330G of the eleventh embodiment is the same as those of the needle-type fluorescence sensor 330 of the sixth embodiment and other needle-type fluorescence sensors except that no filter 314 is present.

The needle-type fluorescence sensor 330G of the present embodiment including the fluorescence sensor 10D, which has a simple structure with no filter 314, can provide the same advantageous effects as those provided by the needle-type fluorescence sensor 330 of the sixth embodiment and the fluorescence sensor 10D.

Variation of Eleventh Embodiment

A needle-type fluorescence sensor 330G2 according to a variation of the eleventh embodiment of the present invention will be described. The needle-type fluorescence sensor 330G2 of the present variation is similar to the needle-type fluorescence sensor 330G of the eleventh embodiment. The same components therefore have the same reference characters and no description thereof will be made.

Since the sensor portion 310G of the needle-type fluorescence sensor 330G of the eleventh embodiment is the fluorescence sensor 10D shown in FIG. 12B and includes the two structurally characteristic PD devices, unwanted excitation light is not detected even without the filter 314. In contrast, a sensor portion 310G of the needle-type fluorescence sensor 330G2 of the present variation includes the filter 314 that cuts off excitation light and structurally characteristic PD devices 312G2, as in the needle-type fluorescence sensor of the eleventh embodiment.

That is, the sensor portion of the needle-type fluorescence sensor 330G2 of the present variation includes the fluorescence sensor 10E according to the variation of the fifth embodiment already described with reference to FIG. 12C and the filter.

The needle-type fluorescence sensor of the present variation including the fluorescence sensor 10E provides the same advantageous effects as those provided by the needle-type fluorescence sensor of the eleventh embodiment and the fluorescence sensor 10E, and hence can detect a fluorescence signal having a more excellent signal-to-noise ratio.

Twelfth Embodiment

A needle-type fluorescence sensor 330H according to a twelfth embodiment of the present invention will be described. The needle-type fluorescence sensor 330H of the present embodiment is similar to the needle-type fluorescence sensor 330 of the sixth embodiment. The same components therefore have the same reference characters and no description thereof will be made.

A sensor portion 310H of the needle-type fluorescence sensor 330H of the present embodiment is the fluorescence sensor 10B of the third embodiment shown in FIG. 10 and includes the Fresnel lens 16C, which is a light collecting section.

The needle-type fluorescence sensor 330H of the present embodiment including the fluorescence sensor 10B shows higher sensitivity than that of the needle-type fluorescence sensor 330 of the sixth embodiment due to the presence of the Fresnel lens 16C, which is a light collecting section, in addition to the advantageous effect provided by the needle-type fluorescence sensor 330.

The present invention is not limited to the embodiments and variations described above, but a variety of changes, modifications, and other improvements can be made to the extent that they do not depart from the spirit of the present invention. Further, the configuration of any of the embodiments and variations described above may be combined with the configuration of any of the other embodiments and variations.

Additional Statements

The fluorescence sensor 10C of the fourth embodiment is configured as follows:

1. A fluorescence sensor including a base member having first and second principal surfaces, a light emitting device that emits excitation light, an indicator layer that interacts with an analyte in a living body under the excitation light to produce fluorescence, and a photoelectric conversion device that converts the fluorescence into an electric signal, wherein the photoelectric conversion device, the light emitting device, and the indicator layer overlap with each other above the first principal surface of the base member.

2. The fluorescence sensor according to the item 1, wherein the base member is a silicon substrate, the indicator layer is disposed above the photoelectric conversion device formed on the first principal surface of the silicon substrate, the light emitting device is disposed above the light indicator layer, and the fluorescence emitted from the analyte having entered the indicator layer through a side surface thereof is incident on the photoelectric conversion device.

3. The fluorescence sensor according to the item 2, further including a filter between the photoelectric conversion device and the indicator layer, wherein the filter reflects and/or absorbs the excitation light having a wavelength shorter than that of the fluorescence and transmits the fluorescence.

4. The fluorescence sensor according to the item 3, wherein the filter is a light absorptive monolayer made of any one of silicon, silicon carbide, and gallium phosphide.

5. The fluorescence sensor according to the item 3, wherein the filter is a multiple interference filter formed of a silicon layer and either a silicon oxide layer or a silicon nitride layer.

6. The fluorescence sensor according to the item 2, wherein the photoelectric conversion device includes a first light receiving portion and a second light receiving portion formed at a deeper level than the level where the first light receiving portion is formed, and detecting a current flowing through either the first or second light receiving portion to which the same bias voltage is applied allows an electric signal representing the incident excitation light to be electrically cut off.

7. The fluorescence sensor according to any one of the items 3 to 6, wherein the light emitting device is a light emitting diode device made of a gallium nitride-based compound semiconductor and formed on a sapphire substrate, and the photoelectric conversion device is formed of a photodiode or a phototransistor.

8. The fluorescence sensor according to any one of the items 3 to 7, further including a light collecting section between the light emitting device and the indicator layer and/or between the filter and the photoelectric conversion device.

9. The fluorescence sensor according to any one of the items 1 to 8, wherein the analyte is a saccharide in blood or a body fluid.

10. The needle-type fluorescence sensor 330F of the tenth embodiment includes a sensor portion, which is the fluorescence sensor according to any one of the items 1 to 9, disposed in a needle distal end portion, a needle body section including a plurality of metal lines disposed from the sensor portion to a needle proximal end portion, and a connector which is integrated with the needle body section and in which the plurality of metal lines extend.

11. The needle-type fluorescence sensor according to the item 10, wherein the connector detachably fits into a body unit that sends information measured by the sensor portion.

12. The needle-type fluorescence sensor according to the item 11, wherein the needle body section further includes a resin substrate or the silicon substrate, a protective layer made of a resin, and the plurality of metal lines.

13. The needle-type fluorescence sensor according to the item 12, wherein the plurality of metal lines are stacked with an insulating layer therebetween to form a multilayer structure.

14. The needle-type fluorescence sensor according to the item 11, wherein the sensor portion, the needle body section, and the connector are monolithically formed from the silicon substrate.

What is claimed is:

1. A fluorescence sensor comprising:
a base member having first and second principal surfaces, the base member comprising silicon;
a photoelectric conversion device formed on the first principal surface of the base member and converts fluorescence into an electrical signal;
a light emitting diode device that emits excitation light, the light emitting diode device disposed above the photoelectric conversion device; and
an indicator layer that interacts with an analyte in a living body under the excitation light to produce fluorescence, the indicator layer disposed above the light emitting diode device;
wherein the photoelectric conversion device, the light emitting diode device, and the indicator layer overlap with each other above the first principal surface of the base member, and the fluorescence produced in the indicator layer passes through the light emitting diode device and impinges on the photoelectric conversion device.

2. The fluorescence sensor according to claim 1,
further comprising a filter between the photoelectric conversion device and the light emitting diode device,
wherein the filter reflects and/or absorbs the excitation light having a wavelength shorter than that of the fluorescence and transmits the fluorescence.

3. The fluorescence sensor according to claim 2,
wherein the filter is a light absorptive monolayer made of any one of silicon, silicon carbide, and gallium phosphide.

4. The fluorescence sensor according to claim 2,
wherein the filter is a multiple interference filter formed of a silicon layer and either a silicon oxide layer or a silicon nitride layer.

5. The fluorescence sensor according to claim 2,
wherein the analyte is a saccharide in blood or a body fluid.

6. The fluorescence sensor according to claim 5,
wherein the light emitting diode device is made of a gallium nitride-based compound semiconductor and formed on a sapphire substrate, and
the photoelectric conversion device is formed of a photodiode or a phototransistor.

7. The fluorescence sensor according to claim 6,
further comprising a light collecting section between the light emitting diode device and the indicator layer and/or between the filter and the photoelectric conversion device.

8. The fluorescence sensor according to claim 2,
wherein the filter is in contact with the light emitting diode device.

9. The fluorescence sensor according to claim 1,
wherein the photoelectric conversion device includes a first light receiving portion and a second light receiving portion to which the same bias voltage as applied to the first light receiving portion is applied, the second light receiving portion formed at a deeper level than the level where the first light receiving portion is formed, and
an electric signal of the incident excitation light is electrically cut off by detecting a current flowing through the second light receiving portion.

10. The fluorescence sensor according to claim 1,
further comprising a light blocking layer above the indicator layer.

11. A needle-type fluorescence sensor that penetrates a living body, the needle-type fluorescence sensor comprising:
a needle body section including a sensor portion disposed in a needle distal end portion that indwells in the living body and a plurality of metal lines disposed from the sensor portion to a needle proximal end portion; and
a connector which is integrated with the needle body section and in which the plurality of metal lines extend,
the sensor portion including
a base member having first and second principal surfaces, the base member comprising silicon,
a photoelectric conversion device that is formed on the first principal surface of the base member and converts fluorescence into an electrical signal;
a light emitting diode device that emits excitation light disposed above the photoelectric conversion device, and
an indicator layer that interacts with an analyte in the living body under the excitation light to produce fluorescence, the indicator layer disposed above the light emitting diode device,
wherein the photoelectric conversion device, the light emitting diode device, and the indicator layer overlap with each other above the first principal surface of the base member, and the fluorescence produced in the indicator layer passes through the light emitting diode device and impinges on the photoelectric conversion device.

12. The needle-type fluorescence sensor according to claim 11,
further comprising a filter between the photoelectric conversion device and the light emitting diode device,
wherein the filter reflects and/or absorbs the excitation light having a wavelength shorter than that of the fluorescence and transmits the fluorescence.

13. The needle-type fluorescence sensor according to claim 12,
wherein the filter is a light absorptive monolayer made of any one of silicon, silicon carbide, and gallium phosphide.

14. The needle-type fluorescence sensor according to claim 12,
wherein the filter is a multiple interference filter formed of a silicon layer and either a silicon oxide layer or a silicon nitride layer.

15. The needle-type fluorescence sensor according to claim 12,
wherein the analyte is a saccharide in blood or a body fluid.

16. The needle-type fluorescence sensor according to claim 15,
wherein the light emitting diode device is made of a gallium nitride-based compound semiconductor and formed on a sapphire substrate, and
the photoelectric conversion device is formed of a photodiode or a phototransistor.

17. The needle-type fluorescence sensor according to claim 16,
wherein the connector detachably fits into a body unit that sends information measured by the sensor portion.

18. The needle-type fluorescence sensor according to claim 17,
wherein the sensor portion further includes a temperature sensor.

19. The needle-type fluorescence sensor according to claim 17,
further comprising a second sensor portion including a second photoelectric conversion device that outputs an electric signal that is not affected by the analyte.

20. The needle-type fluorescence sensor according to claim 17,
wherein the needle body section further includes a resin substrate or the silicon substrate, a protective layer made of a resin, and the plurality of metal lines.

21. The needle-type fluorescence sensor according to claim 20,
wherein the plurality of metal lines are stacked with an insulating layer therebetween to form a multilayer structure.

22. The needle-type fluorescence sensor according to claim 17,
further comprising a light collecting section between the light emitting diode device and the indicator layer and/or between the filter and the photoelectric conversion device.

23. The needle-type fluorescence sensor according to claim 12,
wherein the filter is in contact with the light emitting diode device.

24. The needle-type fluorescence sensor according to claim 11,
wherein the photoelectric conversion device includes a first light receiving portion and a second light receiving portion to which the same bias voltage as applied to the first light receiving portion is applied, the second light receiving portion formed at a deeper level than the level where the first light receiving portion is formed, and
an electric signal of the incident excitation light is electrically cut off by detecting a current flowing through the second light receiving portion.

25. The needle-type fluorescence sensor according to claim 11,
further comprising a light blocking layer above the indicator layer.

26. A method for measuring an analyte by using a fluorescence sensor, the method comprising:
an excitation light irradiation step in which excitation light emitted from a light emitting diode device is introduced into an indicator layer, the indicator layer disposed above the light emitting diode device, the light emitting diode device disposed above a first principal surface of a base member, the base member having a first principal surface and a second principal surface, the base member comprising silicon;

a fluorescence emission step in which the indicator layer interacts with the analyte under the excitation light to produce fluorescence; and a photoelectric conversion step in which the fluorescence produced in the indicator layer passes through the light emitting diode device, impinges on a photoelectric conversion device that is formed on the first principal surface of the base member, and is converted into an electric signal.

27. The method for measuring an analyte according to claim 26, wherein the analyte is a saccharide in blood or a body fluid.

* * * * *